(12) United States Patent
Kuriki et al.

(10) Patent No.: US 7,282,150 B2
(45) Date of Patent: Oct. 16, 2007

(54) METHOD OF EXTRACTING AND METHOD OF PURIFYING AN EFFECTIVE SUBSTANCE

(75) Inventors: Takashi Kuriki, Osaka (JP); Takahisa Nishimura, Nara (JP); Kazuhisa Sugimoto, Osaka (JP)

(73) Assignee: Ezaki Glico Co., Ltd., Osaka (JP)

( * ) Notice: Subject to any disclaimer, the term of this patent is extended or adjusted under 35 U.S.C. 154(b) by 524 days.

(21) Appl. No.: 10/489,639

(22) PCT Filed: Sep. 19, 2002

(86) PCT No.: PCT/JP02/09656

§ 371 (c)(1),
(2), (4) Date: Aug. 19, 2004

(87) PCT Pub. No.: WO03/027049

PCT Pub. Date: Apr. 3, 2003

(65) Prior Publication Data
US 2004/0266999 A1    Dec. 30, 2004

(30) Foreign Application Priority Data
Sep. 20, 2001    (JP)    ............................. 2001-287013
Sep. 20, 2001    (JP)    ............................. 2001-287014

(51) Int. Cl.
*B01D 11/00*    (2006.01)
*C07G 3/00*    (2006.01)

(52) U.S. Cl. ..................... 210/634; 424/736; 426/429; 514/23; 514/25; 536/18.5

(58) Field of Classification Search ................ 210/634, 210/639; 426/427–429, 490, 599, 615, 655–657; 536/8, 18.5, 18.6; 424/195.1, 725, 736; 514/23, 514/24, 53, 54, 25, 26; 435/74, 99, 200, 435/202
See application file for complete search history.

(56) References Cited

U.S. PATENT DOCUMENTS 5,145,781 A * 9/1992 Suzuki et al. .................. 435/99

(Continued)

FOREIGN PATENT DOCUMENTS

EP    0 352 147 A2    1/1990

(Continued)

OTHER PUBLICATIONS

Fonseca et al.; "Critical Assessment of Electrolyte Systems for the Capillary Electrophoresis Analysis of Phenolic Compounds in Herbal Extracts"; *J. Microcolumn Separations*; 13(6), pp. 227-235, 2001.

(Continued)

*Primary Examiner*—Joseph Drodge
(74) *Attorney, Agent, or Firm*—Renner, Otto, Boisselle & Sklar, LLP

(57) ABSTRACT

A method for extracting a hydrophobic group-containing water-soluble organic compound, comprising the step of bringing an aqueous solution containing the hydrophobic group-containing water-soluble organic compound and a saccharide into contact with a polar organic solvent to obtain an aqueous phase and an organic phase, whereby the hydrophobic group-containing water-soluble organic compound is transferred to the organic phase. The saccharide concentration of the aqueous solution may be at least 12 g per 100 ml of the aqueous solution. The aqueous solution may further contain a phase separation assisting agent. The phase separation assisting agent may be selected from the group consisting of sodium chloride, sodium citrate, magnesium sulfate, and ammonium sulfate.

30 Claims, 1 Drawing Sheet

U.S. PATENT DOCUMENTS

| | | | |
|---|---|---|---|
| 5,393,898 A | 2/1995 | Carcasona et al. | 552/262 |
| 6,224,872 B1 * | 5/2001 | Shibuya et al. | 424/729 |
| 6,517,840 B1 * | 2/2003 | Kozak et al. | 424/757 |

FOREIGN PATENT DOCUMENTS

| | | |
|---|---|---|
| EP | 0 920 870 A1 | 6/1999 |
| JP | 48-89882 | 11/1973 |
| JP | 59-210099 | 11/1984 |
| JP | 62-164639 | 7/1987 |
| JP | 01-193280 | 8/1989 |
| JP | 02-129198 | 5/1990 |
| JP | 02-171167 | 7/1990 |
| JP | 04-217629 | 8/1992 |
| JP | 06-284896 | 10/1994 |
| JP | 10-279495 | 10/1998 |
| WO | 01/64606 A1 | 9/2001 |

OTHER PUBLICATIONS

Julkunen-Tiitto; "Phenolic Constituents in the Leaves of Northern Willoss: Methods for the Analysis of Certain Phenolics"; *J. Agric. Food Chem.*; pp. 213-217; 1985.

Bronner; "Extraction and Measurement of Prominent Flavonoids in Orange and Grapefruit Juice Concentrates"; *Journal of Chromatography A*; 705 (1995).

* cited by examiner

METHOD OF EXTRACTING AND METHOD OF PURIFYING AN EFFECTIVE SUBSTANCE

TECHNICAL FIELD

The present invention relates to a method for extracting a hydrophobic group-containing water-soluble organic compound from an aqueous solution containing the hydrophobic group-containing: water-soluble organic compound (e.g., an extract derived from an animal or a plant as well as an enzyme reaction solution) with high purity and high yield.

BACKGROUND ART

As represented by crude drug extracts, a number of natural compounds having a variety of physiological activities are known. These natural compounds are also called physiologically active substances. A number of physiologically active substances are generally purified by conducting extraction using a material containing the physiologically active substance and water, warm water or low-concentration aqueous alcohol solution to obtain an extract solution, concentrating the extract solution, and subjecting the concentrated extract solution to column chromatography. However, such a purifying method requires a large column and equipment accompanying therewith in order to produce a large amount of a physiologically active substance. A small column has very poor efficiency. Therefore, a purified physiologically active substance is very expensive.

Attempts have been made to purify physiologically active substances by a solvent extraction method. However, a method of adding an organic solvent which is inherently immiscible with water, such as ethyl acetate, butanol, and chloroform, to an aqueous solution, stirring, allowing the solution to stand to obtain two phases, i.e., aqueous phase and organic solvent phase, and recovering the physiologically active substance transferred to the organic solvent phase, cannot be used for foods due to safety problems. Even when a physiologically active substance is used for applications other than foods, some physiologically active substances are inefficiently extracted using an organic solvent since the physiologically active substances are not significantly transferred to the organic solvent phase. Since some organic solvents which can be used for foods, such as ethanol and acetone, are miscible with water, these organic solvents cannot be used to extract and purify a physiologically active substance from aqueous solution.

Hesperidin is a representative flavonoid which is contained in orange juice. Flavonoids represented by hesperidin are known to have physiological actions described below, for example. Hesperidin and rutin were previously called vitamin P, and have long been known to have an action that lowers blood pressure (Shintaro Kamiya, Shin-Vitamin-Gaku, [New Vitamin Study] (The Vitamin Society of Japan) 1969, p 439). It has also been reported that hesperidin has the following physiological actions: anti-inflammatory action, analgesic action (E, M. Galati et al., Il Farmaco, 49, 709-712(1994)), antiallergic action (Hideaki Matsuda et al.; Yakugaku Zasshi [Journal of Pharmacology], 111, 193-198 (1991), J. A. Da Silva Emim et al.; J. Pharm. Pharmacol., 46, 118-712(1994)), an action that reduces LDL-cholesterol to ameliorate blood cholesterol levels (M. T. Monforte et al.; Il Farmaco, 50, 595-599(1995)), and carcinostatic action (T. Tanaka, et al.; Cancer Research, 54, 4653-4659(1994), T. Tanaka, et al.; Cancer Research, 57, 246-252(1997), T. Tanaka, et al.: Carcinogenesis, 18, 761-769(1997), T. Tanaka, et al.: Carcinogenesis, 18, 957-965(1997)). Further, in recent studies, it is expected that hesperidin also has an action that promotes differentiation of fat precursor cells to ameliorate conditions, such as diabetes. Diosmin has a vigorous antioxidant activity.

A medical agent containing Diosmin and hesperidin is utilized as a therapeutic drug for venous insufficiency, hemorrhoids, and the like (C. Labrid: Angiology, 45, 524-530(1994)). It has also been reported that hesperidin alone, Diosmin alone, and a mixture of hesperidin and Diosmin suppresses oral cancer, esophageal cancer, colorectal cancer, and the like (T. Tanaka, et al.; Cancer Research, 54, 4653-4659(1994), T. Tanaka, et al.; Cancer Research, 57, 246-252(1997), T. Tanaka, et al.; Carcinogenesis, 18, 761-769 (1997), T. Tanaka, et al.; Carcinogenesis, 18, 957-965 (1997)).

Naringin and neohesperidin are known as bitter substances of citrus, and are used in foods and beverages for the purpose of providing bitterness.

Further, it has been recently revealed that isoflavone effectively improves bone density, suppresses occurrence of breast cancer, and the like (Toda et al. Foods and Ingredients Journal of Japan, No. 172, 83-89 (1997)).

Hesperidin and rutin are inherently insoluble in acetone.

On the other hand, flavonoids, such as hesperidin, naringin, neohesperidin, and rutin, are poorly soluble in water. In order to overcome this drawback, i.e., the poor solubility, attempts have been made to efficiently solubilize these poorly soluble compounds. For example, a method of improving the solubility of flavonoids, such as hesperidin, naringin, neohesperidin, and rutin, by enzymatic glycosylation, is known (Japanese Laid-Open Publication No. 7-107972).

A method of improving the solubility of catechin, caffeic acid, kojic acid, hydroquinone, catechol, resorcinol, protocatechuic acid, gallic acid, vanillin, daidzein, genistein, α-resorcylic acid and phloroglucinol other than the above-described flavonoids by enzymatic glycosylation for the same purpose, is known (Japanese Publication for Opposition No. 7-36758 and T. Nishimura, J. Ferment. Bioeng., 78 (1994) p 37).

However, since the water solubility of the glycoside itself is improved, the glycoside cannot be efficiently extracted in a solvent immiscible with water. Also, due to safety problems, column chromatography, such as adsorption chromatography, is required for purification of glycosides from enzyme reaction solutions in which glycosylation is conducted.

In conventional purification methods, in order to obtain partially purified flavonoids, catechins, phenols and glycosides thereof from natural materials, a method of conducting extraction using the natural material and alkaline aqueous solution, organic solvent, hot water, or the like and then purifying the extract solution by column chromatography, has been employed. However, extraction and purification using a safe organic solvent which can be used for foods are required for obtaining a large amount of these substances with high yield and with low cost. However, since acetone which can be utilized for foods is miscible with water, it is not possible to extract these substances using acetone. Most physiologically active substances which are effective in the food and drug fields have properties such that they are easily soluble in a high polarity solvent, such as water, ethanol, and acetone, while they are poorly soluble in a low polarity solvent, and therefore, cannot be efficiently extracted from a low polarity solvent.

DISCLOSURE OF THE INVENTION

As a result of diligent studies, the present inventors have found that even when using an organic solvent, which is inherently difficult to separate from aqueous phase where the organic solvent is mixed with water or hot water, if a substance having water holding capacity, such as a saccharides is present in an aqueous solution containing a physiologically active substance, it is possible to easily separate aqueous phase from organic phase after mixing and stirring the aqueous solution and the organic solvent. The present inventors also found that the physiologically active substance was transferred to the organic phase. Further, the present inventors found that by increasing the ionic strength of the aqueous solution by adding salt (e.g., sodium chloride and sodium citrate) or an organic acid thereto, an organic solvent which is not otherwise separated from aqueous phase or which is otherwise difficult to separate from aqueous phase even if a saccharide is present can be separated from aqueous phase, and a physiologically active substance can be efficiently transferred to the organic solvent phase. Based on these findings, the present inventors completed the present invention.

The method of the present invention is a method for extracting a hydrophobic group-containing water-soluble organic compound, comprising the step of bringing an aqueous solution containing the hydrophobic group-containing water-soluble organic compound and a saccharide into contact with a polar organic solvent to obtain an aqueous phase and an organic phase, whereby the hydrophobic group-containing water-soluble organic compound is transferred to the organic phase.

In one embodiment, the saccharide concentration of the aqueous solution may be at least 12 g per 100 ml of the aqueous solution.

In one embodiment, the hydrophobic group-containing water-soluble organic compound may be a water-soluble aromatic compound.

In one embodiment, the hydrophobic group-containing water-soluble organic compound may be selected from the group consisting of phenol derivatives and glycosides thereof.

In one embodiment, the hydrophobic group-containing water-soluble organic compound may be selected from the group consisting of hydroquinone glycoside, catechin, salicin, hesperidin, hesperidin glycosides, caffeic acid, salicyl alcohol, and elladitannin.

In one embodiment, the aqueous solution may further contain a phase separation assisting agent.

In one embodiment, the phase separation assisting agent may be a salt or an organic acid.

In one embodiment, the phase separation assisting agent may be selected from the group consisting of sodium chloride, sodium citrate, magnesium sulfate, and ammonium sulfate.

In one embodiment, the polar organic solvent may be tetrahydrofuran or acetonitrile.

In one embodiment, the polar organic solvent may be tetrahydrofuran, acetonitrile, acetone, or isopropyl alcohol.

In one embodiment, the hydrophobic group-containing water-soluble organic compound may be derived from an enzyme reaction solution.

In one embodiment, the enzyme reaction solution may be a glycosylation reaction solution.

In one embodiment, the glycosylation reaction solution may be a hesperidin or hydroquinone glycosylation reaction solution.

In one embodiment, the hydrophobic group-containing water-soluble organic compound may be derived from an organism selected from animals or plants.

In one embodiment the hydrophobic group-containing water-soluble organic compound may be derived from fruit juice.

In one embodiment, the aqueous solution may be prepared by concentrating an enzyme reaction solution containing the hydrophobic group-containing water-soluble organic compound and the saccharide.

In one embodiment, the enzyme reaction solution may be a glycosylation reaction solution.

In one embodiment, the glycosylation reaction solution may be a hesperidin or hydroquinone glycosylation reaction solution.

In one embodiment, the aqueous solution may be prepared by concentrating or diluting an extract of an organism, wherein the extract contains the hydrophobic group-containing water-soluble organic compound and the saccharide, and the organism is an animal or a plant.

In one embodiment, the aqueous solution may be prepared by concentrating fruit juice.

In one embodiment, the aqueous solution may be prepared by adding the phase separation assisting agent to an enzyme reaction solution containing the hydrophobic group-containing water-soluble organic compound and the saccharide, or a concentrate thereof.

In one embodiment, the enzyme reaction solution may be a glycosylation reaction solution.

In one embodiment, the glycosylation reaction solution may be a hesperidin or hydroquinone glycosylation reaction solution.

In one embodiment, the aqueous solution may be prepared by adding the phase separation assisting agent to an extract of an organism, a concentrate thereof, or a diluent thereof, wherein the extract contains the hydrophobic group-containing water-soluble organic compound and the saccharide, and the organism is an animal or a plant.

In one embodiment, the aqueous solution may be prepared by adding the phase separation assisting agent to fruit juice or a concentrate thereof.

The purifying method of the present invention is a method for purifying a phenol derivative glycoside, comprising the steps of bringing a first aqueous solution containing a phenol derivative, a phenol derivative glycoside and a saccharide into contact with a polar organic solvent to obtain a first aqueous phase and an organic phase containing a small amount of water, whereby the phenol derivative and the phenol derivative glycoside are transferred to the organic phase, recovering the organic phase containing the small amount of water, removing the polar organic solvent from the organic phase containing the small amount of water to obtain a second aqueous solution containing the phenol derivative and the phenol derivative glycoside, bringing the second aqueous solution into contact with ethyl acetate to obtain a second aqueous phase and an ethyl acetate phase, whereby the phenol derivative is transferred to the ethyl acetate phase, recovering the second aqueous phase, and concentrating and cooling the second aqueous phase to precipitate the phenol derivative glycoside.

In one embodiment, the phenol derivative and the phenol derivative glycoside may be derived from a phenol derivative glycosylation reaction solution.

In one embodiment, the glycosylation reaction solution may be a hesperidin or hydroquinone glycosylation reaction solution.

In one embodiment, the first aqueous solution may further contain a phase separation assisting agent.

In one embodiment, the glycosylation reaction solution may be a hesperidin or hydroquinone glycosylation reaction solution.

BEST MODE FOR CARRYING OUT THE INVENTION

Figure 1:
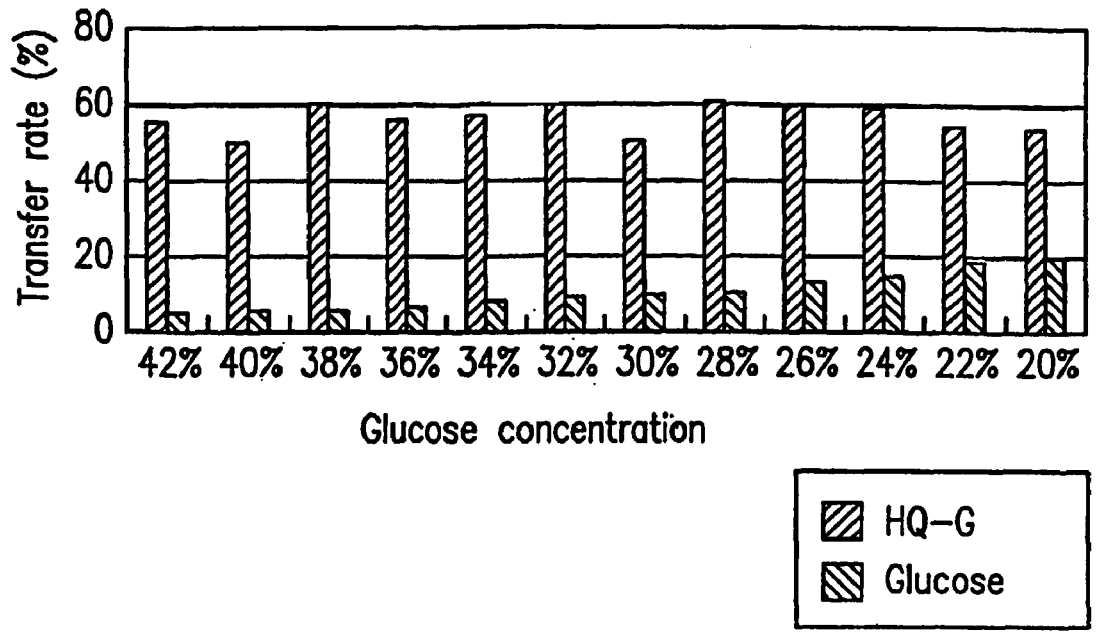
FIG. 1 is a graph showing an influence of glucose concentration on tetrahydrofuran extraction.

Hereinafter, the present invention will be described in detail. As used herein, concentration is represented by grams per 100 cubic centimeters of solution unless otherwise described. For example, "10% sodium chloride solution" refers to a sodium chloride solution in which 10 g of sodium chloride is dissolved per 100 cubic centimeters of solution.

A method according to the present invention is a method of extracting a hydrophobic group-containing water-soluble organic compound. The method of the present invention comprises the step of contacting an aqueous solution containing a hydrophobic group-containing water-soluble organic compound and a saccharide with a polar organic solvent to obtain an aqueous phase and an organic phase so that the hydrophobic group-containing water-soluble organic compound is transferred to the organic phase.

(1) Hydrophobic Group-containing Water-soluble Organic Compound

As used herein, "hydrophobic group-containing water-soluble organic compound" refers to an organic compound which contains a hydrophobic group and is soluble in water.

As used herein, "water-soluble" compound refers to a compound that at least 0.01 g can be dissolved in one liter of water at 20° C. Preferably, at least 0.1 g, more preferably at least 1 g, even more preferably at least 5 g, and most preferably at least 10 g, of a hydrophobic group-containing water-soluble organic compound can be dissolved in one liter of water at 20° C. There is no particular upper limit to the solubility, although the solubility is preferably no more than 300 g in one liter of water at 20° C. More preferably, the solubility is no more than 100 g in one liter of water at 20° C.

A hydrophobic group is preferably a hydrophobic group containing at least three carbon atoms, and more preferably an aromatic residue. Examples of hydrophobic group-containing water-soluble organic compounds include flavonoids, isoflavones, phenolic compounds, flavonoid glycosides, isoflavone glycosides, phenolic compound glycosides, hydroquinone glycosides, anthracene glycosides, water-soluble aromatic compounds (e.g., chalcone glycosides), terpene glycosides, steroid glycosides, triterpenoid glycosides, alkaloid glycosides, and C-glycosides. Preferably, the hydrophobic group-containing water-soluble organic compound is a water-soluble aromatic compound.

As used herein, "water-soluble aromatic compound" refers to a compound which is soluble in water and has an aromatic group.

The water-soluble aromatic compound is preferably selected from the group consisting of phenol derivatives and glycosides thereof.

"Phenol derivative" refers to a compound having a phenol backbone (i.e., a benzene ring) or a flavonoid backbone and having a hydroxyl group linked to the phenol backbone or the flavonoid backbone, including phenol and kojic acid. Examples of the phenol derivative include a compound having a phenolic hydroxyl group on a single phenol or flavonoid backbone, and a compound having at least two phenolic hydroxyl groups on a single phenol or flavonoid backbone. Hereinafter, for the sake of convenience, compounds having one phenolic hydroxyl group on a single phenol or flavonoid backbone are called monophenol type compounds, and compounds having at least two phenolic hydroxyl groups on a single phenol or flavonoid backbone are called polyphenol type compounds.

Compounds having two phenolic hydroxyl groups on a single phenol or flavonoid backbone are called diphenol compounds.

A phenol derivative glycoside having a phenolic hydroxyl group is also included as a phenol derivative.

Examples of monophenol type compounds having one phenolic hydroxyl group on a single phenol or flavonoid backbone include phenol, salicyl alcohol, kojic acid, dimethoxy phenol, acetaminophen, vanillin, and daidzein.

Examples of monophenol compounds also include monophenol type flavonoid type compounds. Examples of monophenol type flavonoid type compounds include monophenol type flavone type compounds, monophenol type isoflavone type compounds, monophenol type flavonol type compounds, monophenol type flavanone type compounds, monophenol type flavanonol type compounds, monophenol type catechin type compounds, monophenol type aurone type compounds, monophenol type chalcone type compounds, and monophenol type dihydrochalcone type compounds.

Examples of dimethoxyphenols include 2,3-dimethoxy phenol, 2,4-dimethoxy phenol, 2,5-dimethoxy phenol, 2,6-dimethoxy phenol, 3,4-dimethoxy phenol, and 3,5-dimethoxy phenol. 3,4-dimethoxy phenol and 3,5-dimethoxy phenol are preferable.

Examples of polyphenol type compounds having at least two phenolic hydroxyl groups on a single phenol or flavonoid backbone include hydroquinone, hesperetin, epigallocatechin, epicatechin gallate, anthocyanidin type compounds, anthocyanin type compounds, caffeic acid, catechol, resorcinol, protocatechuic acid, gallic acid, genistein, β-resorcylic acid, and phloroglucinol.

Examples of diphenol compounds also include diphenol type flavonoid type compounds. Examples of diphenol type flavonoid type compounds include diphenol type flavone type compounds, diphenol type isoflavone type compounds, diphenol type flavonol type compounds, diphenol type flavanone type compounds, diphenol type flavanonol type compounds, diphenol type catechin type compounds, diphenol type aurone type compounds, diphenol type chalcone type compounds, and diphenol type dihydrochalcone type compounds.

Examples of resorcylic acids include α-resorcylic acid, β-resorcylic acid, and γ-resorcylic acid. In the present invention, β-resorcylic acid is preferable.

As used herein, a "phenol derivative glycoside" is a substance in which a phenol derivative moiety is linked to one or more saccharide moiety with glycoside linkage(s). The phenol derivative glycoside may be a mono-glucopyranoside (e.g., hydroquinone-O-α-D-glucopyranoside, salicin, caffeic acid-O-α-D-glucopyranoside, 3,4-dimethoxy phenol-O-α-D-glucopyranoside, and catechin-O-α-D-glucopyranoside), a diglucopyranoside in which a saccharide moiety is additionally linked to the above-described monoglucopyranoside (e.g., a hesperidin derivative), a triglucopyranoside, and the like.

As used herein, a "glycoside" is a substance in which an aglycon is linked to one or more saccharide moieties with glycoside linkage(s). The polymerization degree of the saccharide moiety is preferably 1-10, more preferably 1-5, and even more preferably 1-3. The saccharide moiety can be a monosaccharide moiety or a disaccharide moiety. As used herein, glucosides are included in the definition of the glycoside. Glucosides are glycosides in which one or more glucose moieties are linked to an aglycon.

The hydrophobic group-containing water-soluble organic compound is preferably selected from the group consisting of salicin, coniferin, arbutin, sennoside, stevioside, rubsoside, rutin, hesperidin, naringin, daidzein, genistin, barbaroin, vanillin, saponins, berberine, kaempferol, baicalin, capillarin, catechin, corydaline, esculetin, epicatechin, gingerols, glycyrrhizin, Diosmin, neohesperidin, caffeic acid, salicyl alcohol, elladitannin, and hydroquinone. The hydrophobic group-containing water-soluble organic compound is more preferably selected from the group consisting of hydroquinone glycoside, catechin, salicin, hesperidin, hesperidin glycosides, caffeic acid, salicyl alcohol and elladitannin.

The hydrophobic group-containing water-soluble organic compound may be present in aqueous solution at any concentration. The concentration of the hydrophobic group-containing water-soluble organic compound is preferably 0.01% to 50%, more preferably 0.1% to 40%, even more preferably 0.5% to 30%, still even more preferably 1% to 20%, and most preferably 5% to 15%. If the concentration of the hydrophobic group-containing water-soluble organic compound present in aqueous solution is excessively low, the purification efficiency may be poor. If the concentration of the hydrophobic group-containing water-soluble organic compound present in aqueous solution is excessively high, the hydrophobic group-containing water-soluble organic compound may precipitate. A concentration at which the hydrophobic group-containing water-soluble organic compound does not precipitate is preferable.

The hydrophobic group-containing water-soluble organic compound may be derived from an enzyme reaction solution containing the hydrophobic group-containing water-soluble organic compound. As used herein, an enzyme reaction solution refers to a solution obtained by subjecting any starting material to an enzyme reaction. Examples of such an enzyme reaction solution include a glycosylation reaction solution, a hydrolysis reaction solution, a transfer reaction, and a condensation reaction solution for the hydrophobic group-containing water-soluble organic compound. The enzyme reaction solution preferably contains a saccharide. The enzyme reaction solution is typically a reaction solution after a reaction has proceeded and a reaction product has been produced.

An example of a glycosylation reaction is representatively a glycosyl transfer reaction for a glycosyl transfer acceptor which is catalyzed by cyclodextrin glucanotransferase. Examples of such a glycosyl transfer acceptor include a flavonoid containing a saccharide in the structure thereof, a flavonoid not containing a saccharide in the structure thereof, a phenol compound, and a phenolic compound glycoside. Examples of a representative glycosyl transfer acceptor include hesperidin, naringin, neohesperidin, and rutin.

Another example of the glycosylation reaction is a glycosyl transfer reaction for a glycosyl transfer acceptor, which is catalyzed by a transferring type amylase. Examples of such a glycosyl transfer acceptor include catechin, caffeic acid, kojic acid, hydroquinone, catechol, resorcinol, protocatechuic acid, gallic acid, vanillin, daidzein, genistein, α-resorcylic acid and phloroglucinol.

The glycosylation reaction solution is preferably a glycosylation reaction solution for hesperidin or hydroquinone.

Examples of an enzyme catalyzing an enzyme reaction include, in addition to cyclodextrin glucanotransferase and transferring type amylase, α-amylase, pullulanase, amylomaltase, D-enzyme, neopullulanase, cyclodextrinase, α-glucosidase, cellulase, β-glucosidase, and β-galactosidase.

The enzyme reaction solution containing the hydrophobic group-containing water-soluble organic compound may be designed and obtained by a method known to those skilled in the art.

The hydrophobic group-containing water-soluble organic compound may also be derived from any natural material containing the hydrophobic group-containing water-soluble organic compound. The hydrophobic group-containing water-soluble organic compound may be derived from, for example, an organism (e.g., an animal or a plant). Alternatively, an animal extract or a plant extract can be used. The animal extract refers to any substance extracted from an animal. The plant extract refers to any substance extracted from a plant. For example, any hydrophobic group-containing water-soluble organic compound obtained from a leaf, stem, root, flower, fruit, or the like of a plant can be used. Examples of a plant material include soybean, processed soybean products, sea-cucumber, Chinese nutgall, Scutellaria root (Scutellariae Radix), aloe, Rehmannia root (Rehmanniae Radix), Asiatic ginseng (*Panax ginseng*), Peony root (Paeoniae Radix), Gardenia jasminoides, Glycyrrhiza (Glycyrrhizae Radix), Bupleurum root (Bupleuri Radix), Rhubarb (Rhei rhizome), Houttuyniacordata, Cowberry (*Vaccinium vitis-idaea*), tea, Sweet tea (Chinese blackberry tea; *Rubus suanissm* S.Lee), and citrus (e.g., the fruit of orange). Any hydrophobic group-containing water-soluble organic compound present in the body of an animal can be used.

(2) Saccharides

As used herein, saccharides refer to compounds having the general formula $C_n(H_2O)_m$. Saccharides are grouped into monosaccharides, oligosaccharides, and polysaccharides according to the number of constituents, i.e., saccharide units. In the present invention, monosaccharides and oligosaccharides are preferable. In the present invention, a saccharide, which is soluble in water or, if not, has water holding capacity, is preferable.

Examples of monosaccharides include D-glucose, galactose, fructose, arabinose, xylose, and rhamnose. A preferable monosaccharide is D-glucose.

Oligosaccharides as used herein refer to substances obtained by dehydration-condensation of 2 to 10 monosaccharides. An oligosaccharide has preferably 2 to 9 saccharide units, more preferably 2 to 8 saccharide units, and even more preferably 2 to 7 saccharide units. Examples of oligosaccharide include sucrose, lactose, malto-oligosaccharides, galacto-oligosaccharides, lacto-oligosaccharides, and fructo-oligosaccharides. Examples of the malto-oligosaccharides include maltose, maltotriose, maltotetraose, maltopentaose, and maltohexaose, maltoheptaose, malto-octaose, maltononaose, and maltodecaose. An oligosaccharide may be a straight-chain oligosaccharide or a branched-chain oligosaccharide. An oligosaccharide may have an intramolecular ring structure.

Polysaccharides as used herein refer to substances generated by dehydration-condensation of at least 11 monosaccharides. A polysaccharide preferably has at least one α-1,4 linkage. Examples of polysaccharides include dextrin, amylose, amylopectin, starch, dextran, and cellulose.

Dextrins refer to substances obtained by lowering the molecular weight of starch by a chemical or enzymatic method. Examples of dextrins include British gum, yellow dextrin, white dextrin, PINE-DEX (Matsutani Chemical Industry Co., Ltd.), SUNDECK (Sanwa Cornstarch Co., Ltd.), and Tetrup (Hayashibara Shoji, Inc.).

Amylose is a straight-chain molecule composed of glucose units linked together by α-1,4 linkages. Amylose is contained in natural starch.

Amylopectin is a branched-chain molecule composed of glucose units linked together by α-1,4 linkages to which glucose units are linked together by α-1,6 linkages. Amylopectin is contained in natural starch. As amylopectin, for example, waxy corn starch consisting of 100% amylopectin may be used.

Starch is a mixture of amylose and amylopectin. As starch, any starch which is usually commercially available may be used. The ratio of amylose to amylopectin contained in starch varies depending on the type of plant which produces the starch. The majority of starch contained in waxy rice, waxy corn, and the like is amylopectin. Starch is divided into natural starch, starch degradation products, and processed starch.

Natural starch is divided into tuber starch and cereal starch according to a raw material from which it is derived. Examples of tuber starch include potato starch, tapioca starch, sweet potato starch, kudzu starch, bracken starch, and the like. Examples of cereal starch include corn starch, wheat starch, rice starch, and the like.

Processed starch is starch obtained by subjecting natural starch to treatment, such as hydrolysis, esterification, gelatinization, or the like, to confer properties for better ease of utilization. A wide variety of processed starches are available which have various combinations of properties, such as, for example, temperature at which gelatinization starts, the viscosity of the starch paste, the transparency of the starch paste, aging stability, and the like. There are various types of processed starch. An example of such starch is starch which is obtained by immersing starch granules in acid at a temperature of no more than the gelatinization temperature of the starch so that starch molecules are cleaved but starch granules are not broken.

Starch degradation products are oligosaccharides or polysaccharides obtained by subjecting starch to treatment, such as enzyme treatment, hydrolysis, or the like, which have a lower molecular weight than before the treatment. Examples of the starch degradation products include starch degraded by a debranching enzyme, starch degraded by phosphorylase, and starch partially degraded by hydrolysis.

Starch degraded by a debranching enzyme is obtained by allowing a debranching enzyme to act on starch. By changing the action time of the debranching enzyme to various extents, starch degraded by a debranching enzyme in which branching portions (i.e., α-1,6-glucoside linkage) are cleaved to any extent can be obtained. Examples of the starch degraded by a debranching enzyme include degradation products of 4 to 10,000 saccharide units having 1 to 20α-1,6-glucoside linkages, degradation products of 3 to 500 saccharide units without any α-1,6-glucoside linkages, malto-oligosaccharide, and amylose. In the case of starch degraded by a debranching enzyme, the distribution of the molecular weight of the resultant degradation products may vary depending on the type of starch to be degraded. The starch degraded by a debranching enzyme may be a mixture of saccharide chains having various lengths.

Dextrin and starch partially degraded by hydrolysis refer to degradation products obtained by degrading starch partially by the action of an acid, an alkali, an enzyme, or the like. In the present invention, the number of saccharide units contained in dextrin and starch partially degraded by hydrolysis is preferably about 10 to about 100,000, more preferably about 50 to about 50,000, and even more preferably about 100 to about 10,000. In the case of dextrin and starch partially degraded by hydrolysis, the distribution of the molecular weight of the resultant degradation products may vary depending on the type of starch to be degraded.

Dextrin and the starch partially degraded by hydrolysis may be a mixture of saccharide chains having various lengths.

Dextran refers to α-1,6-glucan.

Cellulose is a straight-chain molecule composed of glucose units linked together by β-1,4-glucoside linkages.

The saccharide may be a single compound or a mixture of a plurality of compounds.

The saccharide may be originally contained in an aqueous solution containing the hydrophobic group-containing water-soluble organic compound, or may be added to an aqueous solution containing the hydrophobic group-containing water-soluble organic compound. The saccharide is preferably originally contained in an aqueous solution containing the hydrophobic group-containing water-soluble organic compound. Examples of such an aqueous solution include the above-described glycosylation reaction solutions and fruit juice.

The saccharide preferably is a small molecule. When a solution contains a relatively high molecular weight polysaccharide, as does a glycosylation reaction solution, an enzyme cleaving saccharide chains, such as glucoamylase, may be added to the solution which is allowed to react, thereby degrading the polysaccharide to monosaccharides or oligosaccharides. It is preferable that a polysaccharide in an aqueous solution is degraded to monosaccharides or oligosaccharides before being brought into contact with an organic solvent. It is preferable that all saccharides are dissolved in an aqueous solution. However, saccharide may be partially suspended in an aqueous solution as long as the saccharide does not interfere with separation of the aqueous solution from an organic solvent.

The saccharide concentration of an aqueous solution may be any concentration. The saccharide concentration of an aqueous solution is preferably at least 12%, more preferably at least 20%, even more preferably at least 30%, still even more preferably at least 40%, and most preferably at least 50%. The upper limit of the saccharide concentration is any concentration as long as the saccharide and the hydrophobic group-containing water-soluble organic compound do not precipitate. For example, the upper limit is no more than 90%, no more than 80%, no more than 70%, no more than 60%, or no more than 55%.

The saccharide concentration of an aqueous solution may be measured by a method known in the art. For example, as a simple method, there is a measuring method using a Brix scale. The measuring method using a Brix scale is simple, but cannot measure each of saccharide separately. In order to measure each of the saccharides separately, for example, an aqueous solution containing saccharides may be subjected to HPLC using a column LiChrosorb $NH_2$ (manufactured by Merck; 4.0×250 mm) and using a mixture of water and acetonitrile at 25:75 (v/v) as a mobile phase, and the eluate may be measured using an RI detector.

The pH of an aqueous solution is preferably 2 to 11, more preferably 3 to 9, and even more preferably 4 to 8.

(3) Polar Organic Solvent

As used herein, "polar organic solvent" refers to an organic solvent which has a solvent strength ($\epsilon^o$) to alumina of at least 0.4 and is miscible with distilled water. The solvent strength of a polar organic solvent is preferably 0.42 to 0.98, more preferably 0.44 to 0.95, and most preferably 0.44 to 0.90. A polar organic solvent may be an organic solvent having a permittivity of at least 7.0 at 20° C. A polar organic solvent preferably has a permittivity of 7.3 to 40.0, more preferably 7.4 to 39.0, and most preferably 7.5 to 38.0 at 20° C.

Examples of the solvent strength to alumina are shown in Table 1. Examples of the permittivity are shown in Table 2. Examples of polar organic solvents used in the present invention include polar organic solvents shown in the following Tables 1 and 2, which have a solvent strength or a permittivity within the above-described ranges.

TABLE 1

| Solvent | Solvent strength to alumina ($\epsilon^o$) |
| --- | --- |
| fluoroalkane | −0.25 |
| n-pentane | 0.00 |
| isooctane | 0.01 |
| hexane | 0.01 |
| n-decane | 0.04 |
| cyclohexane | 0.04 |
| cyclopentane | 0.05 |
| carbon disulfide | 0.15 |
| carbon tetrachloride | 0.18 |
| xylene | 0.26 |
| isopropyl ether | 0.28 |
| toluene | 0.29 |
| benzene | 0.32 |
| ethyl ether | 0.38 |
| chloroform | 0.40 |
| methylene chloride | 0.42 |
| methyl isobutyl ketone | 0.43 |
| tetrahydrofuran | 0.45 |
| ethylene dichloride | 0.49 |
| methyl ethyl ketone | 0.51 |
| acetone | 0.56 |
| dioxane | 0.56 |
| ethyl acetate | 0.58 |
| methyl acetate | 0.60 |
| dimethyl suffixed | 0.62 |
| aniline | 0.62 |
| diethyl amine | 0.63 |
| nitromethane | 0.64 |
| acetonitrile | 0.65 |
| pyridine | 0.71 |
| isopropanol | 0.82 |
| n-propanol | 0.82 |
| ethanol | 0.88 |
| methanol | 0.95 |
| ethylene glycol | 1.11 |
| acetic acid | great |
| water | great |

TABLE 2

| Solvent | e |
| --- | --- |
| isooctane | 1.94 |
| n-hexane | 1.88 |
| n-heptane | 1.92 |
| diethyl ether | 4.33 |
| cyclohexane | 2.02 |
| ethyl acetate | 6.02 |
| toluene | 2.38 |
| chloroform | 4.81 |
| tetrahydrofuran | 7.58 |
| benzene | 2.27 |
| acetone | 20.7 |
| dichloromethane | 8.93 |
| dioxane | 2.25 |
| propanol | 20.33 |
| ethanol | 25.8 |
| dimethylformamide | 36.7 |
| acetonitrile | 37.5 |
| acetic acid | 6.3 |
| dimethyl sulfoxide | 4.7 |
| methanol | 32.7 |
| water | 81.1 | e: permittivity

A polar organic solvent is preferably tetrahydrofuran, isopropanol, acetonitrile, acetone, ethanol, methanol, propanol, pyridine, or dimethoxy sulfoxide, more preferably tetrahydrofuran, isopropanol, acetonitrile or acetone, and most preferably tetrahydrofuran or acetonitrile. When an aqueous solution further contains a phase separation assisting agent, a polar organic solvent is preferably tetrahydrofuran, acetonitrile, acetone or isopropyl alcohol, and more preferably acetone or isopropyl alcohol.

A polar organic solvent is preferably a single compound. However, a mixture of at least two polar organic solvents may be used as long as an organic phase is not separated into two phases. A polar organic solvent, which is appropriate for extraction of a hydrophobic group-containing water-soluble organic compound from an aqueous solution, may be selected by those skilled in the art as required.

The amount of a polar organic solvent which is brought into contact with an aqueous solution is representatively 0.1 to 10 times, and more preferably 0.2 to 2 times the volume of an aqueous solution.

(4) Phase Separation Assisting Agent

An aqueous solution may contain a phase separation assisting agent. As used herein, "phase separation assisting agent" refers to a substance which assists separation of a mixture of an aqueous solution and a polar organic solvent into an aqueous phase and an organic phase. Note that a saccharide and a hydrophobic group-containing water-soluble organic compound are not phase separation assisting agents, even if they have an action of assisting phase separation. A phase separation assisting agent may be a salt having a salting-out effect and a water-soluble substance capable of enhancing ionic strength. A phase separation assisting agent may be a salt or an organic acid. Examples of phase separation assisting agents include, but are not limited to, sulfates (e.g., ammonium sulfate and magnesium sulfate), sodium salts (e.g., sodium chloride and sodium sulfite), phosphates (e.g., potassium phosphate, sodium phosphate, magnesium phosphate, and ammonium phosphate), acetates (e.g., sodium acetate and potassium acetate), lactates (e.g., sodium lactate and magnesium lactate), organic acids (e.g., citric acid, sodium citrate, ascorbic acid, sodium ascorbate, and malic acid), and ammonium chloride. A phase separation assisting agent is preferably a salt and is more preferably selected from the group consisting of sodium chloride, sodium citrate, magnesium sulfate and ammonium sulfate.

A phase separation assisting agent may be contained in an aqueous solution in a sufficient amount to assist phase separation. Such an amount is known to those skilled in the art. The concentration of a phase separation assisting agent contained in an aqueous solution is preferably at least 5%, more preferably 10%, even more preferably at least 15%, and most preferably at least 20%. There is no particular upper limit to the amount of a phase separation assisting agent, although it is preferably no more than 50% and more preferably no more than 40%.

It is preferable that a phase separation assisting agent is contained in an aqueous solution in advance. However, a phase separation assisting agent can be added while an aqueous solution and a polar organic solvent are brought into contact with each other.

(Preparation of an Aqueous Solution Containing a Hydrophobic Group-containing Water-soluble Organic Compound and a Saccharide)

An aqueous solution containing a hydrophobic group-containing water-soluble organic compound and a saccharide may be prepared by a method known to those skilled in the art. Such an aqueous solution may be an enzyme reaction solution which is not subjected to any treatment after the enzyme reaction has proceeded, or an enzyme reaction solution which is concentrated, diluted, filtered, or pH-adjusted after the enzyme reaction has proceeded. Particularly, when the viscosity of an enzyme reaction solution is too high to be stirred, it is preferable to dilute the enzyme reaction solution. Alternatively, an aqueous solution may be prepared by adding a phase separation assisting agent to an enzyme reaction solution containing a hydrophobic group-containing water-soluble organic compound and a saccharide, or a concentrated solution thereof.

An aqueous solution may also be an extract of an organism selected from animals or plants, which contains a hydrophobic group-containing water-soluble organic compound. Such an extract may be prepared by extracting an animal material or a plant material containing a hydrophobic group-containing water-soluble organic compound by a method known in the art. An exemplary extraction method comprises: providing an animal material or a plant material containing a hydrophobic group-containing water-soluble organic compound into an extraction solvent, such as water (e.g., water having a temperature of more than 0° C. and less than 40° C.), warm water (e.g., water having a temperature of no less than 40° C. and less than 60° C.), hot water (e.g., water having a temperature of no less than 60° C. and less than 100° C.), alcohol, pyridine, ethyl acetate, or a mixture thereof; allowing the hydrophobic group-containing water-soluble organic compound to be transferred from the animal material or the plant material to the extraction solvent; removing the animal material and the plant material from the extraction solvent to obtain an extract solution; and concentrating or drying the extract solution if necessary. It is preferable that the extract does not contain an organic solvent. When the extraction solvent is an organic solvent, it is preferable to remove the organic solvent by concentrating the extract solution. The extract may be liquid or solid. Juice obtained by squeezing an animal material or a plant material is also herein included in the definition of an extract. An aqueous solution is preferably fruit juice. An animal material may be the entire animal or any organ or tissue of an animal. A plant material may be the entire plant or any organ (e.g., flower, fruit, seed, root, stem, and leaf) or tissue of a plant. An animal material and a plant material to be subjected to extraction may be either raw or dried. If an extract is an aqueous solution, the extract may be used as it is in the present invention. An aqueous solution may be prepared from an extract by concentration, dilution, or the like. Particularly, when the viscosity of an extract is too high to be stirred, it is preferable to dilute the extract. Note that as long as a hydrophobic group-containing water-soluble organic compound of interest is dissolved in an aqueous solution to be used in the method of the present invention, any other ingredient may be suspended therein. Alternatively, an aqueous solution may be prepared by adding a phase separation assisting agent to an animal extract containing a hydrophobic group-containing water-soluble organic compound and a saccharide, a plant extract containing a hydrophobic group-containing water-soluble organic compound and a saccharide, or a concentrate or diluent of these extracts. For example, an aqueous solution may be prepared by adding a phase separation assisting agent to fruit juice or a concentrate thereof.

An effective ingredient selected from the group consisting of salicin, coniferin, arbutin, sennoside, stevioside, rubsoside, rutin, hesperidin, naringin, daidzein, genistin, barbaroin, vanillin, saponins, berberine, kaempferol, baicalin, capillarin, catechin, corydaline, esculetin, epicatechin, gingerols and glycyrrhizin, is preferably dissolved in an extract solution.

(Extraction of a Hydrophobic Group-containing Water-soluble Organic Compound)

In a method according to the present invention, an aqueous solution containing a hydrophobic group-containing water-soluble organic compound and a saccharide is brought into contact with a polar organic solvent to obtain an aqueous phase and an organic phase, thereby the hydrophobic group-containing water-soluble organic compound is allowed to be transferred to the organic phase.

An aqueous solution and a polar organic solvent may be brought into contact with each other by, for example, mixing the aqueous solution and the polar organic solvent. Bringing an aqueous solution and a polar organic solvent into contact with each other is also called extraction. A temperature at which an aqueous solution and a polar organic solvent are brought into contact with each other is preferably 10° C. to 50° C., more preferably 25° C. to 45° C., even more preferably 20° C. to 40° C., and most preferably 25° C. to 35° C.

An aqueous solution and a polar organic solvent are mixed and stirred, followed by allowing them to stand, resulting in separation to an aqueous phase and an organic phase. In general, the aqueous phase and the organic phase form respective layers, i.e., a water layer and an organic layer. In general, the solvent layer, which has a greater specific gravity, is the lower layer. When an organic solvent which has a smaller specific gravity than that of water is used, the water layer typically is the lower layer while the upper layer is the organic layer.

Typically, an aqueous phase contains a small amount of polar organic solvent, while an organic phase contains a small amount of water. For example, acetone is added to an aqueous solution or a suspension containing a hydrophobic group-containing water-soluble organic compound (e.g., hesperidin and rutin), which are in turn stirred and then allowed to stand. When they are separated into an aqueous phase and an organic phase (acetone phase), a small amount of water is dissolved in the acetone phase. Therefore, compared with the case when water is not contained in the organic phase, the solubility of the hydrophobic group-containing water-soluble organic compound increases, the hydrophobic group-containing water-soluble organic compound is efficiently dissolved in acetone.

When an aqueous solution and a polar organic solvent are mixed to contact each other, the mixture is preferably stirred. Examples of a method for stirring include, but are not limited to, rotating, shaking, and both. In order to efficiently extract and purify a hydrophobic group-containing water-soluble organic compound, a multistage counterflow partition apparatus (also called a continuous liquid-liquid extraction apparatus) can be used.

(Purification of a Phenol Derivative Glycoside)

The method of the present invention is particularly useful for purification of a phenol derivative glycoside. Purification of a phenol derivative glycoside will be described as an example in more detail.

A phenol derivative glycoside may be formed by, for example, causing a saccharide (e.g., a malto-oligosaccharide or starch) to react with a phenol derivative in the presence of an enzyme. Typically, this reaction reaches equilibrium at a certain level and does not proceed further. Therefore, in this enzyme reaction solution, the phenol derivative, the phenol derivative glycoside and the saccharide are present. When the enzyme reaction solution contains a polysaccharide or an oligosaccharide, a glycolytic enzyme, such as glucoamylase, may be added to the enzyme reaction solution, followed by incubation, to degrade the polysaccharide or the oligosaccharide in the enzyme reaction solution to monosaccharides. The degradation of the polysaccharide or the oligosaccharide to monosaccharides increases the mole value, i.e., molar concentration, without changing the total weight of the saccharides, resulting in promotion of separation of an aqueous phase and an organic phase. When the enzyme reaction solution and the polar organic solvent are brought into contact with each other to obtain a first aqueous phase and an organic phase containing a small amount of water, the phenol derivative and the phenol derivative glycoside are transferred to the organic phase. As described above, in order to promote phase separation, a phase separation assisting agent may be added to the aqueous phase to obtain an aqueous solution containing the phase separation assisting agent, and then the aqueous solution may be brought into contact with the polar organic solvent.

Thereafter, the organic phase containing a small amount of water is recovered. A phenol derivative and a phenol derivative glycoside contain a hydrophobic portion which causes them to have a higher affinity to an organic phase than that of a saccharide. Therefore, the phenol derivative and the phenol derivative glycoside are efficiently transferred to the organic phase, the saccharide is less transferred to the organic phase. Therefore, the phenol derivative and the phenol derivative glycoside are extracted in the recovered organic phase. In general, assuming that the same total amount of a polar organic solvent is used for partition extraction, if the polar organic solvent is divided into some aliquots and the aliquots are used to perform extraction from an aqueous solution a plurality of times, the efficiency of the extraction is greater than when the whole amount of the polar organic solvent is used a single time to contact the aqueous solution for extraction. Therefore, a step of bringing an aqueous phase remaining after an organic phase is recovered into contact with a polar organic solvent to obtain an aqueous phase and an organic phase containing a small amount of water again and recovering the organic phase, may be performed twice or more. The recovery operation of an organic phase is performed at least twice, the obtained organic phases may be combined together and may be used in a subsequent step.

Thereafter, the polar organic solvent is removed from the organic phase containing a small amount of water. A method for removing the polar organic solvent from the organic phase may be any method known to those skilled in the art. Examples of such a method include concentration using an evaporator and evapor. The polar organic solvent may be completely removed, or may remain in a small amount as long as it does not interfere with a subsequent step. After the removal of the polar organic solvent, the phenol derivative and the phenol derivative glycoside remain in a small amount of water which has been contained in the polar organic solvent. In this removal step, it is preferable to avoid much water from being removed. In this removal step, it is preferable that the phenol derivative and the phenol derivative glycoside do not precipitate. If the phenol derivative and the phenol derivative glycoside precipitate, it is preferable that the phenol derivative and the phenol derivative glycoside are dissolved by addition of water. Thus, a second aqueous solution containing the phenol derivative and the phenol derivative glycoside is obtained.

Thereafter, the second aqueous solution is brought into contact with ethyl acetate to obtain a second aqueous phase and an ethyl acetate phase, so that the phenol derivative is transferred to the ethyl acetate phase.

Thereafter, the second aqueous phase is recovered. Since the phenol derivative does not contain a glycoside moiety, the phenol derivative has a higher affinity to the ethyl acetate phase than that of the phenol derivative glycoside. Therefore, the phenol derivative is efficiently transferred to the ethyl acetate phase, while the phenol derivative glycoside is less transferred to the ethyl acetate phase. Therefore, the phenol derivative glycoside remains in the recovered aqueous phase. When a small amount of saccharide remains in the second solution, the saccharide remains in the aqueous phase. As in the step of contacting the aqueous solution and the polar organic solvent and the step of recovering the organic phase, a step of bringing the aqueous phase remaining after the removal of the ethyl acetate phase into contact with ethyl acetate to obtain an aqueous phase and an ethyl acetate phase again and recovering the second aqueous phase may be performed at least twice.

Note that although a method is herein described in which the step of contacting an organic phase with ethyl acetate is performed after the step of contacting the aqueous solution and the polar organic solvent and the step of recovering the organic phase, the aqueous solution may be brought into contact with ethyl acetate and an aqueous phase is recovered before the aqueous phase is brought into contact with a polar organic solvent.

Thereafter, the second aqueous phase is concentrated and cooled so as to precipitate the phenol derivative glycoside. It is preferable to concentrate the second aqueous phase so that the phenol derivative glycoside in the second aqueous phase reaches a concentration of at least 10%, preferably at least 15%, more preferably at least 20%, and most preferably at least 25%. This is done by utilizing the fact that the saturation concentration in water of a phenol derivative glycoside is lower than the saturation concentration in water of a saccharide. For example, assuming that the saccharide is glucose and the phenol derivative glycoside is hydroquinone glycoside, the fact that the saturation concentration in water of glucose is about 18% and the saturation concentration in water of hydroquinone glycoside is about 10% is utilized.

EXAMPLES

Next, the present invention will be described in more detail by way of examples, although the present invention is not limited to the examples.

Experimental Example 1

Influence of a Saccharide on Phase Separation

Glucose, sucrose and fructose were used as representatives of respective types of saccharide so that an influence thereof on phase separation of an aqueous solution and a polar organic solvent could be studied.

Specifically, glucose, sucrose or fructose was dissolved in water to prepare 10%, 15%, 20%, 25%, 30% and 50% aqueous solutions. 10 ml of acetonitrile or tetrahydrofuran was added to 10 ml of each aqueous saccharide solution, followed by vigorous stirring using a separating funnel for 5 minutes. Both acetonitrile and tetrahydrofuran are polar organic solvents which are water miscible and when they are mixed with water, the mixture does not undergo separation into an aqueous phase and an organic phase. After the stirring, the mixture was allowed to stand for 30 minutes, observing whether or not the mixture was separated into two phases, an aqueous phase and an organic phase. The results from the addition of tetrahydrofuran or acetonitrile to each aqueous solution are shown in Tables 3 to 5. In the tables, THF represents tetrahydrofuran and AcCN represents acetonitrile.

TABLE 3

| | Glucose | | | | | |
|---|---|---|---|---|---|---|
| | 50% | 30% | 25% | 20% | 15% | 10% |
| AcCN | Yes | Yes | Yes | Yes | Yes | No |
| THF | Yes | Yes | Yes | No | No | No |

Yes: Separated
No: Not separated

TABLE 4

| | Sucrose | | | | | |
|---|---|---|---|---|---|---|
| | 50% | 30% | 25% | 20% | 15% | 10% |
| AcCN | Yes | Yes | Yes | Yes | Yes | No |
| THF | Yes | No | No | No | No | No |

Yes: Separated
No: Not separated

TABLE 5

| | Fructose | | | | | |
|---|---|---|---|---|---|---|
| | 50% | 30% | 25% | 20% | 15% | 10% |
| AcCN | Yes | Yes | Yes | Yes | Yes | No |
| THF | Yes | Yes | No | No | No | No |

Yes: Separated
No: Not separated

As shown in Tables 3 to 5, it was found that when acetonitrile or tetrahydrofuran was mixed with the aqueous saccharide solution, when a certain amount of saccharide was present, phase separation occurred.

According to the results, it was found that adjustment of the type and concentration of a saccharide contained in an aqueous solution would facilitate phase separation and, for example, it is preferable to adjust a saccharide concentration of at least about 12%.

Experimental Example 2

Influence of a Salt on Phase Separation

Next, an influence of a salt on phase separation was studied.

Specifically, sodium chloride was added to an aqueous glucose solution having a glucose concentration of 25% or 50% to a concentration of 20% or 10%, respectively, to prepare a sodium chloride-containing aqueous glucose solution. 10 ml of acetone or isopropanol, which is a polar organic solvent, was added to 10 ml of each aqueous solution, followed by vigorous stirring using a separating funnel 5 minutes. After stirring, the mixture was allowed to stand for 30 minutes, observing whether the mixture was separated into two phases. The results are shown in Table 6.

TABLE 6

| | Glucose 50% + NaCl 20% | Glucose 25% + NaCl 10% |
|---|---|---|
| Acetone | Yes | No |
| 2-ProOH | Yes | Yes |

Yes: Separated
No: Not separated

Sodium citrate was added to an aqueous solution having a dextrin concentration of 25%, to a concentration of 20% to prepare a sodium citrate-containing aqueous dextrin solution. Note that dextrin is a PINE-DEX #1 manufactured by Matsutani Chemical Industry Co., Ltd., which has DE of 7 to 9. As used herein, "DE" is an index which shows the degree of degradation of a starch and is a percentage of direct reducing saccharide converted to glucose in the solid content. Magnesium sulfate was added to an aqueous solution having a glucose concentration of 25% to a concentration of 10% to prepare an aqueous magnesium sulfate-containing glucose solution. 10 ml of acetone, which is a polar organic solvent, was added to 10 ml of each aqueous solution, followed by vigorous stirring using a separating agent for 5 minutes. After stirring, the mixture was allowed to stand for 30 minutes, observing whether the mixture was separated into two phases. The results are shown in Table 7.

TABLE 7

| | Dextrin 25% + Sodium Citrate 20% | Glucose 25% + Magnesium Sulfate 10% |
|---|---|---|
| Acetone | Yes | Yes |

Yes: Separated
No: Not separated

As shown in Tables 6 and 7, when the sodium chloride-containing aqueous glucose solution, the sodium citrate-containing aqueous dextrin solution and the magnesium sulfate-containing aqueous glucose solution were respectively mixed with acetone or isopropanol, phase separation occurred. The addition of a salt, such as sodium chloride, sodium citrate, or magnesium sulfate, could lead to the occurrence of phase separation in a polar organic solvent which does not otherwise undergo phase separation in the case of 50% aqueous saccharide solution. As a result, it was found that a salt, such as sodium chloride, acts as a phase separation assisting agent. It is believed that a salt acts as a phase separation assisting agent by increasing the ionic strength of an aqueous solution in which the salt is dissolved. Therefore, any substance which can increase ionic strength is considered to be able to be used as a phase separation assisting agent.

Example 1

Extraction of Catechins

Example 1a 1 g of a mixture of catechins (SUNPHENON®; manufactured by Taiyo Kagaku Co., Ltd.) was dissolved in 100 ml of an aqueous solution containing 30% glucose to obtain a sample aqueous solution. The absorbance at 280 nm of the sample aqueous solution was measured. 10 ml of tetrahydrofuran was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of the catechins extracted in the upper phase (polar organic solvent phase) was calculated from a reduction in the absorbance at 280 nm of the lower phase and the solution volume of the lower phase. As a result, it was found that by a single extraction operation, 94.1% of the starting amount of catechins was extracted in the tetrahydrofuran phase.

Example 1b

This additional extraction operation to Example 1a was conducted except for use of 10 ml of acetonitrile instead of 10 ml of tetrahydrofuran. As a result, it was found that by a single extraction operation, 84.4% of the starting amount of catechins was extracted in the acetonitrile phase.

Example 2

Extraction of Catechins

Example 2a 1 g of a mixture of catechins (SUNPHENON®; manufactured by Taiyo Kagaku) was dissolved in 100 ml of an aqueous solution containing 30% glucose and 10% sodium chloride to obtain a sample aqueous solution. The absorbance at 280 nm of the sample aqueous solution was measured. 10 ml of acetone was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of the catechins extracted in the upper phase (polar organic solvent phase) was calculated from a reduction in the absorbance at 280 nm of the lower phase and the solution volume of the lower phase. As a result, it was found that by a single extraction operation, 91.8% of the starting amount of catechins was extracted in the acetone phase.

Example 2b

This additional extraction operation to Example 2a was conducted except for use of 10 ml of isopropanol instead of 10 ml of acetone. As a result, it was found that by a single extraction operation, 93.2% of the starting material of catechins was extracted in the isopropanol phase.

Example 3

Extraction of Hesperidin Glycosides

Example 3a 1 g of hesperidin glycosides (manufactured by Toyo Sugar Refining Co., Ltd.) were dissolved in 100 ml of an aqueous solution containing 30% glucose to obtain a sample aqueous solution. The absorbance at 280 nm of the sample aqueous solution was measured. 10 ml of tetrahydrofuran was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of hesperidin glycosides extracted in the upper phase (polar organic solvent phase) was calculated from a reduction in the absorbance at 280 nm of the lower phase and the solution volume of the lower phase. As a result, it was found that by a single extraction operation, 50.0% of the starting amount of hesperidin glycosides was extracted in the tetrahydrofuran phase. Further, similar operations and measurements were performed twice more by adding 5 ml of tetrahydrofuran to the aqueous phase recovered after the tetrahydrofuran extraction. As a result, it was found that a total of 80.0% of the hesperidin glycosides was extracted.

Example 3b

This additional extraction operation to Example 3a was conducted except for use of 10 ml of acetonitrile instead of 10 ml of tetrahydrofuran. As a result, it was found that by a single extraction operation, 27.6% of the starting amount of hesperidin glycosides was extracted in the acetonitrile phase.

Example 4

Extraction of Hesperidin Glycosides

Example 4a 1 g of hesperidin glycosides (Toyo Sugar Refining Co., Ltd.) were dissolved in 100 ml of an aqueous solution containing 30% glucose and 10% sodium chloride to obtain a sample aqueous solution. The absorbance at 280 nm of the sample aqueous solution was measured. 10 ml of acetone was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of hesperidin glycosides extracted in the upper phase (polar organic solvent phase) was calculated from a reduction in the absorbance at 280 nm of the lower phase and the solution volume of the lower phase. As a result, it was found that by a single extraction operation, 43.5% of the starting amount of hesperidin glycosides was extracted in the acetone phase. Further, similar operations and measurements were performed twice more by adding 5 ml of acetone to the aqueous phase recovered after the acetone extraction.

As a result, it was found that a total of 90.0% of the hesperidin glycosides was extracted.

Example 4b

This additional extraction operation to Example 4a was conducted except for use of 10 ml of isopropanol instead of 10 ml of acetone. As a result, it was found that by a single extraction operation, 32.0% of the starting amount of hesperidin glycosides was extracted in the isopropanol phase.

Example 5

Extraction of Salicin

Example 5a 1 g of salicin was dissolved in 100 ml of an aqueous solution containing 30% glucose to obtain a sample aqueous solution. The absorbance at 280 nm of the sample aqueous solution was measured. 10 ml of tetrahydrofuran was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of salicin extracted in the upper phase (polar organic solvent phase) was calculated from a reduction in the absorbance at 280 nm of the lower phase and the solution volume of the lower phase. As a result, it was found that by a single extraction operation, 96.5% of the starting amount of salicin was extracted in the tetrahydrofuran phase.

Example 5b

This additional extraction operation to Example 5a was conducted except for use of 10 ml of acetonitrile instead of 10 ml of tetrahydrofuran. As a result, it was found that by a single extraction operation, 98.1% of the starting amount of salicin was extracted in the acetonitrile phase.

Example 6

Extraction of Salicin

Example 6a 1 g of salicin was dissolved in 100 ml of an aqueous solution containing 30% glucose and 10% sodium chloride to obtain a sample aqueous solution. The absorbance at 280 nm of the sample aqueous solution was measured. 10 ml of acetone was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of salicin extracted in the upper phase (polar organic solvent phase) was calculated from a reduction in the absorbance at 280 nm of the lower phase and the solution volume of the lower phase. As a result, it was found that by a single extraction operation, 58.0% of the starting amount of salicin was extracted in the acetone phase.

Example 6b

This additional extraction operation to Example 6a was conducted except for use of 10 ml of isopropanol instead of 10 ml of acetone. As a result, it was found that by a single extraction operation, 97.0% of the starting amount of salicin was extracted in the isopropanol phase.

Example 7

Extraction of Caffeic Acid

Example 7a 1 g of caffeic acid was dissolved in 100 ml of an aqueous solution containing 30% glucose to obtain a sample aqueous solution. The absorbance at 280 nm of the sample aqueous solution was measured. 10 ml of tetrahydrofuran was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of caffeic acid extracted in the upper phase (polar organic solvent phase) was calculated from a reduction in the absorbance at 280 nm of the lower phase and the solution volume of the lower phase. As a result, it was found that by a single extraction operation, 88.6% of the starting amount of caffeic acid was extracted in the tetrahydrofuran phase.

Example 7b

This additional extraction operation to Example 7a was conducted except for use of 10 ml of acetonitrile instead of 10 ml of tetrahydrofuran. As a result, it was found that by a single extraction operation, 76.2% of the starting amount of caffeic acid was extracted in the acetonitrile phase.

Example 8

Extraction of Caffeic Acid

Example 8a 1 g of caffeic acid was dissolved in 100 ml of an aqueous solution containing 30% glucose and 10% sodium chloride to obtain a sample aqueous solution. The absorbance at 280 nm of the sample aqueous solution was measured. 10 ml of acetone was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of caffeic acid extracted in the upper phase (polar organic solvent phase) was calculated from a reduction in the absorbance at 280 nm of the lower phase and the solution volume of the lower phase. As a result, it was found that by a single extraction operation, 78.2% of the starting amount of caffeic acid was extracted in the acetone phase.

Example 8b

This additional extraction operation to Example 8a was conducted except for use of 10 ml of isopropanol instead of 10 ml of acetone. As a result, it was found that by a single extraction operation, 87.2% of the starting amount of caffeic acid was extracted in the isopropanol phase.

Example 9

Extraction of Salicyl Alcohol

Example 9a 1 g of salicyl alcohol was dissolved in 100 ml of an aqueous solution containing 30% glucose to obtain a sample aqueous solution. The absorbance at 280 nm of the sample aqueous solution was measured. 10 ml of tetrahydrofuran was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of salicyl alcohol extracted in the upper phase (polar organic solvent phase) was calculated from a reduction in the absorbance at 280 nm of the lower phase and the solution volume of the lower phase. As a result, it was found that by a single extraction operation, 98.7% of the starting material of salicyl alcohol was extracted in the tetrahydrofuran phase.

Example 9b

This additional extraction operation to Example 9a was conducted except for use of 10 ml of acetonitrile instead of 10 ml of tetrahydrofuran. As a result, it was found that by a single extraction operation, 98.2% of the starting amount of salicyl alcohol was extracted in the acetonitrile phase.

Example 10

Extraction of Salicyl Alcohol

Example 10a 0.1 g of salicyl alcohol was dissolved in 100 ml of an aqueous solution containing 30% glucose and 10% sodium chloride to obtain a sample aqueous solution. The absorbance at 280 nm of the sample aqueous solution was measured. 10 ml of acetone was added to 10 ml of the sample aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of salicyl alcohol extracted in the upper phase (polar organic solvent phase) was calculated from a reduction in the absorbance at 280 nm of the lower phase and the solution volume of the lower phase. As a result, it was found that by a single extraction operation, 87.7% of the starting amount of salicyl alcohol was extracted in the acetone phase.

Example 10b

This additional extraction operation to Example 10a was conducted except for use of 10 ml of isopropanol instead of 10 ml of acetone. As a result, it was found that by a single extraction operation, 98.7% of the starting amount of salicyl alcohol was extracted in the isopropanol phase.

Example 11

Extraction of Elladitannin and Polymers Thereof

Example 11a

An aqueous sweet tea extract solution (SUNTENCHA; manufactured by Suntory Ltd.) was diluted two-fold with water to obtain a two-fold diluent. Glucose and sodium chloride were added and dissolved in the two-fold diluent to concentrations of 10% and 10%, respectively to obtain an aqueous solution. The absorbance at 280 nm of the aqueous solution was measured. 20 ml of acetone was added to 20 ml of the aqueous solution, followed by vigorous stirring using a separating funnel for 5 minutes. Thereafter, the mixture was allowed to stand for 30 minutes. As a result, the mixture was separated into two phases. The lower phase (aqueous phase) was recovered, and the volume and the absorbance at 280 nm thereof were measured. The amount of effective ingredients (i.e., elladitannin and polymers thereof) extracted in the upper phase (polar organic solvent phase) was calculated from a reduction in the absorbance at 280 nm of the lower phase and the solution volume of the lower phase. As a result, it was found that by a single extraction operation, 43.1% of the effective ingredients were extracted in the acetone phase. Moreover, the level of coloration in the acetone phase was about ⅓ that of the aqueous phase. Thus, it was found that by the extraction operation, the effective ingredients were extracted and the decolorization effect was obtained.

Example 12

Extraction of Hesperidin from Fruit Juice 10 ml of 15% sodium chloride solution was added to 10 ml of California orange juice concentrate (five-fold concentrate), and stirred to homogeneity, thereby obtaining an aqueous solution. The amount of hesperidin in the California orange juice concentrate used was measured by HPLC using a column ODS, where the mobile phase was a mixture of acetonitrile and water at 20:80, the flow rate was 0.5 ml/min, and the column temperature was 40° C. The absorbance of the eluate was detected at 280 nm. A specific method of detecting the amount of hesperidin is described in Japanese Laid-Open Publication No. 8-80177. 20 ml of acetone was added to 20 ml of the resultant aqueous solution, followed by vigorous stirring using a separating funnel for 5 minutes. Thereafter, the mixture was allowed to stand for 30 minutes. As a result, the mixture was separated into two phases. The upper phase (polar organic solvent phase) was recovered, and the volume thereof was measured. The amount of hesperidin was measured by HPLC as described above. As a result, by a single extraction operation, 75% of hesperidin was extracted in the acetone phase.

Example 13

Extraction of Hesperidin from Glycosylation Reaction Solution

An aqueous solution in which 5% soluble starch (manufactured by Merck) and 0.5% hesperidin were dissolved was adjusted with hydrochloric acid to pH 9.0. Alkaline-resistant CGTase (described in Japanese Laid-Open Publication No. 7-107972) was added to the aqueous solution to a concentration of 5 units/ml. Thereafter, an enzyme reaction was allowed to proceed at 37° C. for 16 hours. After the end of the enzyme reaction, a portion of the enzyme reaction solution was collected, and the amounts of hesperidin and hesperidin glycosides were measured by a HPLC analysis method. In the HPLC analysis method, LiChrospher 100RP18 (Merck; 4.0×250 mm) column was used, where the mobile phase was a mixture of acetonitrile and water at 20:80, the flow rate was 0.5 ml/min, and the column temperature was 40° C. The absorbance of the eluate was detected at 280 nm. A method of analyzing hesperidin and hesperidin glycosides is described in Japanese Laid-Open Publication No. 8-80177. As a result, it was found that due to the enzyme reaction, about 80% of the hesperidin which was added at the start of the reaction was converted into hesperidin glycosides.

Thereafter, glucose and sodium chloride were added and dissolved in the enzyme reaction solution after the enzyme reaction to concentration of 20% and 10%, respectively, to obtain a glucose and sodium chloride-containing enzyme reaction solution. An equal volume of acetone was added to the glucose and sodium chloride-containing enzyme reaction solution, followed by vigorous stirring using a separating funnel for 5 minutes. The mixture was allowed to stand for 30 minutes. As a result, the mixture was separated into two phases. The upper acetone phase was collected, and the volume thereof was measured, and the amount of hesperidin glycosides dissolved in the acetone phase was measured by HPLC as described above. As a result, about 45% of the hesperidin glycosides present in the enzyme reaction solution after the end of the enzyme reaction was extracted in the acetone phase. Further, an amount of acetone, which was half the volume of the enzyme reaction solution, was added to the lower aqueous phase, stirred, and allowed to stand, and the upper phase was recovered. This additional extraction operation was carried out three times. As a result, all of the hesperidin glycosides could be recovered.

Example 14

Extraction of Hydroquinone Glycoside from Glycosylation Reaction Solution

An aqueous solution, in which 35% dextrin (PINE-DEX #1 where DE is 7 to 9; manufactured by Matsutani Chemical Industry Co., Ltd.) and 15% hydroquinone were dissolved, was adjusted with SN sodium hydroxide aqueous solution to pH 6.5. A glycosylation enzyme (amylase X-23 described in Japanese Laid-Open Publication No. 6-277053) was added to the aqueous solution to a concentration of 20 units/ml. Thereafter, incubation was performed at 45° C. for 40 hours to cause a hydroquinone glycosylation reaction. After the end of the enzyme reaction, a portion of the enzyme reaction solution was collected, and the amounts of hydroquinone and hydroquinone glycoside were measured by a HPLC analysis method. In the HPLC analysis method, LiChrospher 100RP18 (Merck; 4.0×250 mm) column was used, where the mobile phase was a mixture of water, methanol and phosphoric acid at 80:19.7:0.3 (v/v), the flow rate was 0.5 ml/min, and the column temperature was 40° C. The amounts of hydroquinone and hydroquinone glycoside in the eluate were detected by ultraviolet spectroscopy. The amount of product malto-oligosaccharide was measured by a HPLC analysis method using the enzyme reaction solution. In the HPLC analysis method, LiChrosorb NH$_2$ (Merck; 4.0×250 mm) column was used, where the mobile phase was a mixture of water and acetonitrile at 25:75, the flow rate was 1.0 ml/min, and the column temperature was 40° C. Malto-oligosaccharide in the eluate was detected by a RI detector. As a result, it was found that due to the enzyme reaction, about 35% of the hydroquinone was converted into hydroquinone glycoside, and the dextrin was degraded to glucose and malto-oligosaccharides. Further, glucoamylase (manufactured by Nagase Chemtex; brand name XL-4) was added to the enzyme reaction solution after the end of the enzyme reaction to a concentration of 8.8 units/ml, followed by incubation at 45° C. for 3 hours, thereby degrading the oligosaccharides in the enzyme reaction solution to glucose.

Thereafter, an equal volume of tetrahydrofuran was added to the enzyme reaction solution after the end of the degradation of the oligosaccharides, followed by vigorous stirring using a separating funnel for 5 minutes. The mixture was allowed to stand for 30 minutes. As a result, the mixture was separated into two phases. The upper tetrahydrofuran phase was recovered, and the volume thereof was measured. The amount of hydroquinone glycoside dissolved in the tetrahydrofuran phase was analyzed by HPLC as described above. As a result, about 65% of the hydroquinone glycoside present in the enzyme reaction solution after the end of the enzyme reaction was extracted in the tetrahydrofuran phase. Further, an amount of tetrahydrofuran, which was half the volume of the enzyme reaction solution, was added to the lower aqueous phase, stirred, and allowed to stand, and the upper phase was recovered. This additional extraction operation was carried out three times. As a result, all of the hydroquinone glycoside could be recovered.

Example 15

Extraction of Hydroquinone Glycoside from Glycosylation Reaction Solution

An aqueous solution, in which 35% dextrin (PINE-DEX #1 where DE is 7 to 9; manufactured by Matsutani Chemical Industry Co., Ltd.) and 15% hydroquinone were dissolved, was adjusted with 5N sodium hydroxide aqueous solution to pH 6.5. A glycosylation enzyme (amylase X-23 described in Japanese Laid-Open Publication No. 6-277053) was added to the aqueous solution to a concentration of 20 units/ml. Thereafter, incubation was performed at 45° C. for 40 hours to cause a hydroquinone glycosylation reaction. After the end of the enzyme reaction, a portion of the enzyme reaction solution was collected, and the amounts of hydroquinone and hydroquinone glycoside were measured by a HPLC analysis method. In the HPLC analysis method, LiChrospher 100RP18 (Merck; 4.0×250 mm) column was used, where the mobile phase was a mixture of water, methanol and phosphoric acid at 80:19.7:0.3 (v/v), the flow rate was 0.5 ml/min, and the column temperature was 40° C. The amounts of hydroquinone and hydroquinone glycoside in the eluate were detected by ultraviolet spectroscopy. The amount of product malto-oligosaccharide was measured by a HPLC analysis method using the enzyme reaction solution. In the HPLC analysis method, LiChrosorb NH$_2$ (Merck; 4.0×250 mm) column was used, where the mobile phase was a mixture of water and acetonitrile at 25:75, the flow rate was 1.0 ml/min, and the column temperature was 40° C. Malto-oligosaccharide in the eluate was detected by a RI detector. As a result, it was found that due to the enzyme reaction, about 35% of the hydroquinone was converted into hydroquinone glycoside, and the dextrin was degraded to glucose and malto-oligosaccharides. Further, glucoamylase (manufactured by Nagase Chemtex; brand name XL-4) was added to the enzyme reaction solution after the end of the enzyme reaction to a concentration of 8.8 units/ml, followed by incubation at 45° C. for 3 hours, thereby degrading the oligosaccharides in the enzyme reaction solution to glucose.

Thereafter, the enzyme reaction solution after the degradation of the oligosaccharides was vacuum concentrated by a factor of about 1.4 using an evaporator. Ammonium sulfate was added to the concentrate to a concentration of 20% to obtain an ammonium sulfate-containing concentrate. An equal volume of acetone was added to the ammonium sulfate-containing concentrate, followed by vigorous stirring using a separating funnel for 5 minutes. The mixture was allowed to stand for 30 minutes. As a result, the mixture was separated into two phases. The upper acetone phase was recovered, and the volume thereof was measured. The amount of hydroquinone glycoside dissolved in the acetone phase was analyzed by HPLC as described above. As a result, about 60% of the hydroquinone glycoside present in the enzyme reaction solution after the end of the enzyme reaction was extracted in the acetone phase. Further, an amount of acetone, which was 0.8 times the volume of the concentrate, was added to the lower aqueous phase, stirred, and allowed to stand, and the upper phase was recovered. This additional extraction operation was carried out three times. As a result, all of the hydroquinone glycoside could be recovered.

Example 16

Extraction of Hydroquinone Glycoside from Glycosylation Reaction Solution

An aqueous solution, in which 35% dextrin (PINE-DEX #1 where DE is 7 to 9; manufactured by Matsutani Chemical Industry Co., Ltd.) and 15% hydroquinone were dissolved, was adjusted with 5N sodium hydroxide aqueous solution to pH 6.5. A glycosylation enzyme (amylase X-23 described in Japanese Laid-Open Publication No. 6-277053) was added to the aqueous solution to a concentration of 20 units/ml. Thereafter, incubation was performed at 45° C. for 40 hours to cause a hydroquinone glycosylation reaction. After the end of the enzyme reaction, a portion of the enzyme reaction solution was collected, and the amounts of hydroquinone and hydroquinone glycoside were measured by a HPLC analysis method. In the HPLC analysis method, LiChrospher 100RP18 (Merck; 4.0×250 mm) column was used, where the mobile phase was a mixture of water, methanol and phosphoric acid at 80:19.7:0.3 (v/v), the flow rate was 0.5 ml/min, and the column temperature was 40° C. The amounts of hydroquinone and hydroquinone glycoside in the eluate were detected by ultraviolet spectroscopy. The amount of product malto-oligosaccharide was measured by a HPLC analysis method using the enzyme reaction solution. In the HPLC analysis method, LiChrosorb $NH_2$ (Merck; 4.0×250 mm) column was used, where the mobile phase was a mixture of water and acetonitrile at 25:75, the flow rate was 1.0 ml/min, and the column temperature was 40° C. Malto-oligosaccharide in the eluate was detected by a RI detector. As a result, it was found that due to the enzyme reaction, about 35% of the hydroquinone was converted into hydroquinone glycoside, and the dextrin was degraded to glucose and malto-oligosaccharides. Further, glucoamylase (manufactured by Nagase Chemtex; brand name XL-4) was added to the enzyme reaction solution after the end of the enzyme reaction to a concentration of 8.8 units/ml, followed by incubation at 45° C. for 3 hours, thereby degrading the oligosaccharides in the enzyme reaction solution to glucose.

Thereafter, an equal volume of acetonitrile was added to the enzyme reaction solution after the degradation of the oligosaccharides, followed by vigorous stirring using a separating funnel for 5 minutes. The mixture was allowed to stand for 1 hour. As a result, the mixture was separated into two phases. The upper acetonitrile phase was recovered, and the amount thereof was measured. The amount of hydroquinone glycoside dissolved in the acetonitrile phase was analyzed by HPLC as described above. As a result, about 30% of the hydroquinone glycoside present in the enzyme reaction solution after the end of the enzyme reaction was extracted in the acetonitrile phase. Further, a volume of acetonitrile, which was equal to the volume of the enzyme reaction solution, was added to the lower aqueous phase, stirred, and allowed to stand, and the upper phase was recovered. This additional extraction operation was carried out five times. As a result, about 90% of the hydroquinone glycoside which was present in the enzyme reaction solution after the end of the enzyme reaction could be recovered.

Example 17

Study of Conditions for Glucoamylase Treatment

When a glycosylation enzyme reaction is conducted using dextrin or starch as a starting material, a large amount of glucose and dextrin having a lower molecular weight than that of a starting material is present in the enzyme reaction solution after the end of the reaction. Even if the concentration of overall saccharides is the same, the higher the mole value, the lesser the transfer of saccharide to an organic phase. Therefore, in order to efficiently degrade dextrin remaining after the end of the glycosylation enzyme reaction to glucoses, conditions for the degradation reaction of dextrin were studied.

An aqueous solution, in which 35% dextrin (PINE-DEX #1 where DE is 7 to 9; manufactured by Matsutani Chemical Industry Co., Ltd.) and 15% hydroquinone were dissolved, was adjusted with 5N sodium hydroxide aqueous solution to pH 6.5. A glycosylation enzyme (amylase X-23 described in Japanese Laid-Open Publication No. 6-277053) was added to the aqueous solution to a concentration of 20 units/ml. Thereafter, incubation was performed at 45° C. for 40 hours to cause a hydroquinone glycosylation reaction.

1.4 µl (1-fold amount), 2.1 µl (1.5-fold amount) or 2.8 µl (2-fold amount) of glucoamylase (manufactured by Nagase Chemtex; brand name XL-4) was added to 1 ml of the glycosylation reaction solution after the end of the reaction. Thereafter, the mixture was incubated at 45° C. for 3 or 4 hours. After the incubation, the contents of glucose and maltose in the solution were confirmed by a HPLC analysis method. In the HPLC analysis method, LiChrosorb $NH_2$ (Merck; 4.0×250 mm) column was used, where the mobile phase was a mixture of water and acetonitrile at 25:75, the flow rate was 1.0 ml/mm, and the column temperature was 40° C. Glucose and maltose in the eluate were detected by a RI detector. The amounts of hydroquinone and hydroquinone glycoside in the eluate were detected by a HPLC analysis method. In the HPLC analysis method, LiChrospher 100RP18 (Merck; 4.0×250 mm) column was used, where the mobile phase was a mixture of water, methanol and phosphoric acid at 80:19.7:0.3 (v/v), the flow rate was 0.5 ml/min, and the column temperature was 40° C. The amounts of hydroquinone and hydroquinone glycoside in the eluate were detected by ultraviolet spectroscopy. Based on the resultant amounts of the obtained hydroquinone and hydroquinone glycoside (HQG), the hydroquinone glycosylation rate was calculated. The results are shown in Table 8 below.

TABLE 8

| Samples | Glucose concentration (%) | | Maltose concentration (%) | | HQG glycosylation rate (%) | |
| --- | --- | --- | --- | --- | --- | --- |
| | 3 hrs | 4 hrs | 3 hrs | 4 hrs | 3 hrs | 4 hrs |
| (XL-4) 1-fold | 11.6 | 12.2 | 5.2 | 4.9 | 36.1 | 36.2 |
| (XL-4) 1.5-fold | 13.9 | 14.7 | 4.2 | 3.7 | 36.1 | 36.2 |
| (XL-4) 2-fold | 15.2 | 15.8 | 3.0 | 2.6 | 36.1 | 36.2 |

Even when saccharide degradation was performed using the 1-fold amount of glucoamylase for 3 or 4 hours, the enzyme reaction solution had substantially the same composition as before the addition of glucoamylase. Therefore, it was suggested that with 1-fold glucoamylase, extension of a reaction by about one or two hours is not likely to dramatically reduce the amount of maltose.

Further, even if the amount of glucoamylase was increased, the glycosylation rate was not substantially changed. This indicates that glucoamylase can degrade dextrin without degrading hydroquinone glycoside which is a product of interest. Therefore, it was found that for promotion of dextrin degradation, an increase in the amount of glucoamylase is more effective than extension of degradation reaction time.

Next, an influence of a difference between glucoamylase treatments on THF treatment was studied. 1 ml of (XL-4) treatment solution and 1 ml of THF were mixed together, followed by vigorous shaking using a separating funnel for 1 minute. After shaking, the mixture was allowed to stand for 1 hour. As a result, the mixture was separated into two phases. The aqueous phase was recovered. Water was added to the aqueous phase to 1 ml. The amounts of glucose and maltose were measured by an HPLC analysis method using the aqueous phase. In the HPLC analysis method, LiChrosorb NH$_2$ (Merck; 4.0×250 mm) column was used, where the mobile phase was a mixture of water and acetonitrile at 25:75, the flow rate was 1.0 ml/min, and the column temperature was 40° C. Glucose and maltose in the eluate were detected by a RI detector. The amounts of hydroquinone and hydroquinone glycoside in the eluate were measured by a HPLC analysis method. In the HPLC analysis method, LiChrospher 100RP18 (Merck; 4.0×250 mm) column was used, where the mobile phase was a mixture of water, methanol and phosphoric acid at 80: 19.7:0.3 (v/v), the flow rate was 0.5 ml/mm, and the column temperature was 40° C. The amounts of hydroquinone and hydroquinone glycoside in the eluate were measured by ultraviolet spectroscopy. Based on the obtained results and the above-described glucose concentration, maltose concentration and HQG concentration before extraction with THF, the extraction rate to the THF phase was calculated. The results are shown in Table 9 below.

TABLE 9

| | Extraction rate to THF (%) | | |
| --- | --- | --- | --- |
| Samples | Glucose | Maltose | HQG |
| (XL-4) 1-fold | 43.3 | 38.6 | 71.2 |
| (XL-4) 1.5-fold | 36.3 | 33.0 | 70.0 |
| (XL-4) 2-fold | 38.0 | 36.4 | 73.7 |

As a result, it was confirmed that as the glucose concentration was increased by the glucoamylase treatment, the extraction of glucose to the THF phase tended to be suppressed.

A tendency was also confirmed, in which the larger the amount of glucoamylase added to the sample, the smaller the volume of the aqueous phase recovered after shaking with THF and separation (the smaller the amount of water transferred to the THF phase).

Example 18

Influence of Saccharide Concentration on Extraction to a Tetrahydrofuran Phase

An influence of glucose concentration in an aqueous solution on extraction to a tetrahydrofuran (THF) phase was studied.

Initially, an aqueous solution containing 42% glucose and 9% hydroquinone glycoside was prepared. This aqueous solution was serially diluted with water to prepare aqueous solutions having glucose concentrations from 40% to 20%. Needless to say, by the dilution of the aqueous solution, not only glucose but also hydroquinone glycoside was diluted. 5 ml of THF was added to 5 ml of the thus-prepared aqueous solution, followed by stirring at 30° C. for 5 minutes using a mixer. After the stirring, the mixture was centrifuged at 3000 rpm for 5 minutes. The upper phase was recovered. As the glucose concentration decreased, the amount of the THF phase was lessened. When the glucose concentration was 20%, phase separation did not occur by a single extraction operation. 5 ml of THF was added to the lower phase again and then the upper phase was similarly recovered. The two upper phases obtained for the aqueous solutions was added together. The contents of glucose and maltose were measured by a HPLC analysis method. In the HPLC analysis method, LiChrosorb NH$_2$ (Merck; 4.0×250 mm) column was used, where the mobile phase was a mixture of water and acetonitrile at 25:75, the flow rate was 1.0 ml/min, and the column temperature was 40° C. Glucose and maltose in the eluate were detected by a RI detector. The amounts of hydroquinone and hydroquinone glycoside in the eluate were detected by a HPLC analysis method. In the HPLC analysis method, LiChrospher 100RP18 (Merck; 4.0×250 mm) column was used, where the mobile phase was a mixture of water, methanol and phosphoric acid at 80:19.7: 0.3 (v/v), the flow rate was 0.5 ml/min, and the column temperature was 40° C. The amounts of hydroquinone and hydroquinone glycoside in the eluate were measured by ultraviolet spectroscopy.

The results are shown in FIG. 1. As can be seen from FIG. 1, the transfer rate of hydroquinone glycoside was not much dependent on the glucose concentration. However, the transfer rate of glucose decreased with an increase in the glucose concentration. Accordingly, it was found that if the saccharide concentration of an aqueous solution for use in extraction is increased, the transfer of a saccharide to a polar organic solvent phase is less than the transfer of a hydrophobic group-containing water-soluble organic compound, whereby a high-purity hydrophobic group-containing water-soluble organic compound can be obtained.

Example 19

Influence of Concentration of Glycosylation Reaction Solution on Extraction of Hydroquinone Glycoside As shown in the above-described Example 18, it was found that if the saccharide concentration of an aqueous solution is increased, the transfer of the saccharide to an organic phase is suppressed, so that a hydrophobic group-containing water-soluble organic compound is efficiently transferred to the organic phase. Therefore, it was confirmed whether or not by concentrating an enzyme reaction solution containing a hydrophobic group-containing water-soluble organic compound, the transfer of a saccharide to an organic phase was suppressed, so that the extraction efficiency of the hydrophobic group-containing water-soluble organic compound was increased.

An aqueous solution, in which 35% dextrin (PINE-DEX #1 where DE is 7 to 9; manufactured by Matsutani Chemical Industry Co., Ltd.) and 15% hydroquinone were dissolved, was adjusted with 5N sodium hydroxide aqueous solution to pH 6.5. A glycosylation enzyme (amylase X-23 described in Japanese Laid-Open Publication No. 6-277053) was added to the aqueous solution to a concentration of 20 units/ml. Therefore, incubation was performed at 45° C. for 40 hours to cause a hydroquinone glycosylation reaction. 2.1 µl (1.5-fold amount) of glucoamylase (manufactured by Nagase Chemtex; brand name XL-4) was added per ml of the glycosylation reaction solution after the end of the reaction. Thereafter, glucoamylase treatment was performed at 45° C. for 4 hours, thereby obtaining a reaction solution.

5 ml of this reaction solution was condensed by an evaporator to be concentrated to 80% (4.0 ml) or 70% (3.5 ml) by volume. An equal volume of THF was added to an unconcentrated reaction solution, the 80% concentrate or the 70% concentrate, followed by vigorous shaking using a mixer for 1 minute. Extraction was conducted under a condition of 30° C. The mixture was allowed to stand for 1 hour. The mixture was separated into two phases. The upper THF phase was recovered. The resultant THF phase was analyzed by HPLC as described above for the contents of glucose, maltose and hydroquinone glycoside. A step of adding an amount of THF, which was 0.5 times the amount of the aqueous phase, to the lower aqueous phase again, shaking, extraction, and recovering the upper THF phase, was further repeated twice. The obtained THF phases were combined together. Note that although an intermediate layer was generated in the concentrate during the phase separation, the intermediate layer was included in the aqueous phase. The results are shown in the following Tables 10 to 12.

TABLE 10

Unconcentrated amylase treatment reaction solution
(Brix concentration of two-fold diluent (Bx) = 24.5)

| Samples | Volume of solution (ml) | Corrected concentration (equivalent in 5 ml) % | | | Extraction rate (%) | | |
|---|---|---|---|---|---|---|---|
| | | Glucose | Maltose | HQG | Glucose | Maltose | HQG |
| Unconcentrated amylase treatment reaction solution | 5 | 18.8 | 1.7 | 10.8 | | | |
| THF phase total | 9.5 | 7.4 | 0.1 | 9.9 | 39.2 | 3.2 | 90.9 |

TABLE 11

80% concentrate (two-fold diluent Bx = 29.5)
(glucose 22.7%, maltose: 1.3%, HQG: 13.5%)

| Samples | Volume of solution (ml) | Corrected concentration (equivalent in 5 ml) % | | | Extraction rate (%) | | |
|---|---|---|---|---|---|---|---|
| | | Glucose | Maltose | HQG | Glucose | Maltose | HQG |
| GA treatment solution 80% concentrate | 4 | 18.2 | 1.1 | 10.8 | | | |
| THF phase total | 9.2 | 4.7 | 0 | 10.9 | 26.1 | 0 | 101.1 |

TABLE 12

| | 70% concentrate (two-fold diluent Bx = 34.0) (glucose 25.8%, maltose: 1.9%, HQG: 15.2%) | | | | | | |
|---|---|---|---|---|---|---|---|
| | Volume of solution | Corrected concentration (equivalent in 5 ml) % | | | Extraction rate (%) | | |
| Samples | (ml) | Glucose | Maltose | HQG | Glucose | Maltose | HQG |
| GA treatment solution 70% concentrate | 3.5 | 18 | 1.3 | 10.6 | | | |
| THF phase total | 7.7 | 3.9 | 0 | 10.1 | 21.7 | 0 | 95.2 |

As a result, as expected, by performing THF extraction after concentrating the post-glucoamylase treatment reaction solution, the amount of glucose extracted in the THF phase could be suppressed to about 50% to 60% of that extracted from the unconcentrated solution.

Example 20

Influence of a Hydrophobic Group-containing Water-soluble Organic Compound on Phase Separation As described in Example 17, when a glycosylation reaction solution was subjected to extraction using THF, an aqueous phase was completely separated from the organic phase even if the glucose concentration was no more than 20%, and the THF phase was larger than that of the aqueous phase. On the other hand, in the above-described Example 18, when a solution containing 42% glucose and 9% hydroquinone glycoside (containing substantially no hydroquinone) was diluted with water to a glucose concentration of 20%, phase separation was not obtained in spite of addition of THF. Therefore, an influence of a hydrophobic group-containing water-soluble organic compound on phase separation was investigated.

Hydroquinone was added to a 20% glucose-containing diluent as prepared in the above-described Example 18, to a concentration of 10%, thereby obtaining an aqueous solution. An equal volume of THF was added to the aqueous solution, followed by stirring using a mixer for 5 minutes. Thereafter, the mixture was allowed to stand for 1 hour. As a result, a THF phase was completely separated from the aqueous phase. Moreover, water got mixed in the THF phase, so that the THF phase was larger than the aqueous phase. The THF phase was recovered. The content of a hydroquinone glycoside in THF was measured by HPLC as described above. As a result, it was found that a larger amount of hydroquinone glycoside was extracted than when hydroquinone was not added. The reason is believed to be that by adding a substance well soluble in a THF phase, such as hydroquinone, to an aqueous phase, THF is not easily transferred to the aqueous phase, so that separation was more efficient and a high concentration of hydroquinone was dissolved in THF so that the hydroquinone promoted the transfer of the glycoside.

Example 21

Influence of Temperature on Extraction to a Tetrahydrofuran Phase

The influence of temperature on extraction to a tetrahydrofuran phase was investigated.

Initially, an aqueous solution, in which 35% dextrin (PINE-DEX #1 where DE is 7 to 9; manufactured by Matsutani Chemical Industry Co., Ltd.) and 15% hydroquinone were dissolved, was adjusted with 5N sodium hydroxide aqueous solution to pH 6.5. A glycosylation enzyme (amylase X-23 described in Japanese Laid-Open Publication No. 6-277053) was added to the aqueous solution to a concentration of 20 units/ml. Thereafter, incubation was performed at 45° C. for 40 hours to cause a hydroquinone glycosylation reaction. After the end of the reaction, 2.1 µl (1.5-fold amount) of glucoamylase (manufactured by Nagase Chemtex; brand name XL-4) was added to each 1 ml of the glycosylation reaction solution. Thereafter, the mixture was incubated at 45° C. for 4 hours to obtain a post-glucoamylase treatment reaction solution.

5 ml of THF was added to 5 ml of the post-glucoamylase treatment reaction solution, followed by stirring using a mixer at 3, 10, 22, or 45° C. for 5 minutes. Thereafter, the mixture was centrifuged at 3000 rpm for 5 minutes. As a result, the mixture was separated into two phases. The aqueous phase was recovered. Water was added to the aqueous phase to a volume of 5 ml to obtain an aqueous solution. After the adjustment, the hydroquinone, hydroquinone glycoside and glucose concentrations of the aqueous solution were measured by HPLC as described above.

The results are shown in Table 13.

TABLE 13

| | the hydroquinone, hydroquinone glycoside and glucose concentrations of the aqueous phase | | | | | | |
|---|---|---|---|---|---|---|---|
| | Start | 3° C. | 10° C. | 20° C. | 22° C. | 30° C. | 45° C. |
| HQ | 9.5 | 0.9 | 0.7 | 1.0 | 1.0 | 1.0 | 1.2 |
| HQG | 11.5 | 2.8 | 2.7 | 3.4 | 3.5 | 3.5 | 4.8 |
| Glucose | 19.4 | 11.1 | 11.5 | 13.3 | 13.4 | 13.4 | 16.6 | unit: %

Figure 2:
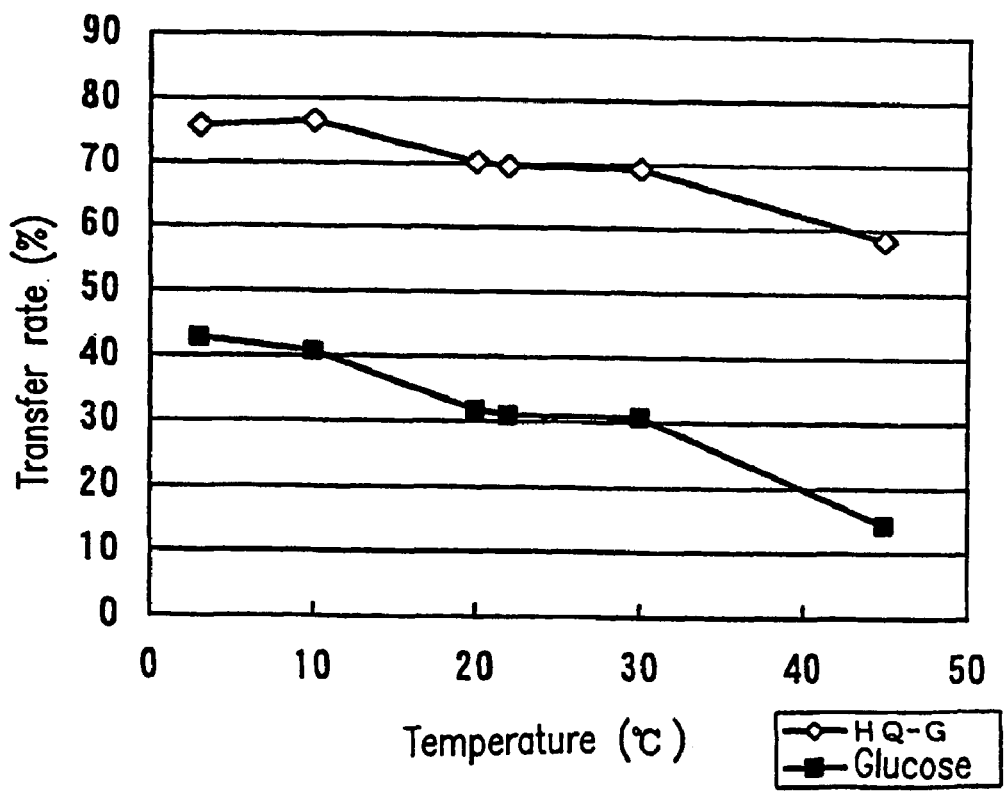
FIG. 2 is a graph showing the transfer rates of hydroquinone glycoside and glucose to a tetrahydrofuran phase.

Based on the results in Table 13, the transfer rate of hydroquinone glycoside and glucose were calculated. FIG. 2 shows a graph of the transfer rate.

As can be seen from Table 13 and FIG. 2, when the extraction temperature was low, a large amount of saccharide was transferred to the THF phase. As the temperature was increased, the transfer rates of hydroquinone, hydroquinone glycoside and glucose to the THF phase were decreased. The reason is believed to be that the solubility of HQG and glucose to the aqueous phase increased with an increase in temperature, so that the transfer to the THF phase was decreased. Further, the higher the temperature, the larger the difference between the transfer rates of hydroquinone glycoside and glucose. Therefore, it was found that the purity of hydroquinone glycoside can be more increased by performing extraction at as high a temperature as possible.

INDUSTRIAL APPLICABILITY

According to the present invention, a method of extracting a hydrophobic group-containing water-soluble organic compound is provided. The extracting method and the purifying method of the present invention can be used as a technique for extracting and purifying an effective ingredient from various animals and plants, or as a technique of extracting and purifying an effective ingredient from various enzyme reaction solutions. According to the method of the present invention, a hydrophobic group-containing water-soluble organic compound can be easily and inexpensively separated and purified.

The invention claimed is:

1. A method for extracting a hydrophobic group-containing water-soluble organic compound, comprising the step of:
    bringing an aqueous solution containing the hydrophobic group-containing water-soluble organic compound and a saccharide into contact with a polar organic solvent to obtain an aqueous phase and an organic phase, whereby the hydrophobic group-containing water-soluble organic compound is transferred to the organic phase;
    wherein the hydrophobic group-containing water-soluble organic compound is selected from the group consisting of hydroquinone glycoside, catechin, hesperidin, hesperidin glycosides, caffeic acid, salicyl alcohol, and elladitannin; and
    wherein the polar organic solvent is tetrahydrofuran or acetonitrile.

2. A method according to claim 1, wherein the saccharide concentration of the aqueous solution is at least 12 g per 100 ml of the aqueous solution.

3. A method according to claim 1, wherein the amount of the polar organic solvent is 0.2 to 2 times the volume of the aqueous solution.

4. A method according to claim 1, wherein the hydrophobic group-containing water-soluble organic compound is derived from an enzyme reaction solution.

5. A method according to claim 4, wherein the enzyme reaction solution is a glycosylation reaction solution.

6. A method according to claim 5, wherein the glycosylation reaction solution is a hesperidin or hydroquinone glycosylation reaction solution.

7. A method according to claim 1, wherein the hydrophobic group-containing water-soluble organic compound is derived from an organism selected from animals or plants.

8. A method according to claim 1, wherein the hydrophobic group-containing water-soluble organic compound is derived from fruit juice.

9. A method according to claim 1, wherein the aqueous solution is prepared by concentrating an enzyme reaction solution containing the hydrophobic group-containing water-soluble organic compound and the saccharide.

10. A method according to claim 9, wherein the enzyme reaction solution is a glycosylation reaction solution.

11. A method according to claim 10, wherein the glycosylation reaction solution is a hesperidin or hydroquinone glycosylation reaction solution.

12. A method according to claim 1, wherein the aqueous solution is prepared by concentrating or diluting an extract of an organism, wherein the extract contains the hydrophobic group-containing water-soluble organic compound and the saccharide, and the organism is an animal or a plant.

13. A method according to claim 1, wherein the aqueous solution is prepared by concentrating fruit juice.

14. A method for purifying a phenol derivative glycoside, comprising the steps of:
    bringing a first aqueous solution containing a phenol derivative, a phenol derivative glycoside and a saccharide into contact with a polar organic solvent to obtain a first aqueous phase and an organic phase containing a small amount of water, whereby the phenol derivative and the phenol derivative glycoside are transferred to the organic phase;
    recovering the organic phase containing the small amount of water;
    removing the polar organic solvent from the organic phase containing the small amount of water to obtain a second aqueous solution containing the phenol derivative and the phenol derivative glycoside;
    bringing the second aqueous solution into contact with ethyl acetate to obtain a second aqueous phase and an ethyl acetate phase, whereby the phenol derivative is transferred to the ethyl acetate phase;
    recovering the second aqueous phase; and
    concentrating and cooling the second aqueous phase to precipitate the phenol derivative glycoside;
    wherein the phenol derivative and the phenol derivative glycoside are derived from a phenol derivative glycosylation reaction solution;
    wherein the glycosylation reaction solution is a hesperidin or hydroquinone glycosylation reaction solution; and
    wherein the polar organic solvent is tetrahydrofuran or acetonitrile.

15. A method according to claim 14, wherein the amount of the polar organic solvent is 0.2 to 2 times the volume of the first aqueous solution.

16. A method according to claim 14, wherein the glycosylation reaction solution is a hydroquinone glycosylation reaction solution.

17. A method for extracting a hydrophobic group-containing water-soluble organic compound, comprising the steps of:
    bringing an aqueous solution containing the hydrophobic group-containing water-soluble organic compound and a saccharide into contact with a polar organic solvent to obtain an aqueous phase and an organic phase, wherein the hydrophobic group-containing water-soluble organic compound is transferred to the organic phase; and
    separating and recovering the organic phase from the aqueous phase,
    wherein the hydrophobic group-containing water-soluble organic compound is selected from the group consisting of hydroquinone glycoside, catechin, hesperidin, hesperidin glycosides, caffeic acid, salicyl alcohol, and elladitannin; and
    wherein the polar organic solvent is tetrahydrofuran or acetonitrile.

18. A method according to claim 17, further comprising removing at least a portion of the polar organic solvent from the organic phase.

19. A method according to claim 17, wherein the saccharide concentration of the aqueous solution is at least 12 g per 100 ml of the aqueous solution.

20. A method according to claim 17, wherein the amount of the polar organic solvent is 0.2 to 2 times the volume of the aqueous solution.

21. A method according to claim 17, wherein the hydrophobic group-containing water-soluble organic compound is derived from an enzyme reaction solution.

22. A method according to claim 21, wherein the enzyme reaction solution is a glycosylation reaction solution.

23. A method according to claim 22, wherein the glycosylation reaction solution is a hesperidin or hydroquinone glycosylation reaction solution.

24. A method according to claim 17, wherein the hydrophobic group-containing water-soluble organic compound is derived from an organism selected from animals or plants.

25. A method according to claim 17, wherein the hydrophobic group-containing water-soluble organic compound is derived from fruit juice.

26. A method according to claim 17, wherein the aqueous solution is prepared by concentrating an enzyme reaction solution containing the hydrophobic group-containing water-soluble organic compound and the saccharide.

27. A method according to claim 26, wherein the enzyme reaction solution is a glycosylation reaction solution.

28. A method according to claim 27, wherein the glycosylation reaction solution is a hesperidin or hydroquinone glycosylation reaction solution.

29. A method according to claim 17, wherein the aqueous solution is prepared by concentrating or diluting an extract of an organism, wherein the extract contains the hydrophobic group-containing water-soluble organic compound and the saccharide, and the organism is an animal or a plant.

30. A method according to claim 17, wherein the aqueous solution is prepared by concentrating fruit juice.

* * * * *